(12) United States Patent
Bard et al.

(10) Patent No.: US 8,680,363 B2
(45) Date of Patent: Mar. 25, 2014

(54) INSECT RESISTANT AND HERBICIDE TOLERANT SOYBEAN EVENT 9582.814.19.1

(75) Inventors: Nathan Bard, Edgerton, WI (US); Gregory A. Bradfisch, Carmel, IN (US); Yunxing C. Cui, Carmel, IN (US); James E. Dripps, Carmel, IN (US); Thomas Hoffman, Zionsville, IN (US); Dayakar Pareddy, Carmel, IN (US); Dawn M. Parkhurst, Avon, IN (US); Sandra G. Toledo, West Lafayette, IN (US); Barry Wiggins, Westfield, IN (US); Ning Zhou, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/559,177

(22) Filed: Jul. 26, 2012

(65) Prior Publication Data

US 2013/0061346 A1   Mar. 7, 2013

Related U.S. Application Data

(60) Provisional application No. 61/511,664, filed on Jul. 26, 2011, provisional application No. 61/521,798, filed on Aug. 10, 2011.

(51) Int. Cl.
*C12N 15/82* (2006.01)
*A01H 1/00* (2006.01)
*A01H 5/10* (2006.01)
*A01H 5/00* (2006.01)

(52) U.S. Cl.
USPC ........... 800/265; 800/260; 800/266; 800/267; 800/278; 800/279; 800/295; 800/298; 800/300; 800/312

(58) Field of Classification Search
None
See application file for complete search history.

(56) References Cited

U.S. PATENT DOCUMENTS

| 4,808,426 A * | 2/1989 | Strop et al. .................. 426/417 |
| 2004/0031072 A1 | 2/2004 | La Rosa et al. |
| 2007/0044171 A1 | 2/2007 | Kovalic et al. |
| 2007/0271630 A1 | 11/2007 | Boukharov et al. |
| 2009/0191636 A1 | 7/2009 | Ramage et al. |

OTHER PUBLICATIONS

Hohe et al, A tool for understanding homologous recombination in plants, Plant Cell Rep. (2003) 21:1135-1142.*
Spencer et al, Segregation of transgenes in maize, Plant Mol. Biol. (1992) 18:201-210.*
DeMaagd et al, How *Bacillus thuringiensis* has evolved specific toxins to colonize the insect world, Trends Gen. (2001) 17:193-199.*
Walker et al, Field evaluation of soybean engineered with a synthetic Cry1Ac transgene for resistant to corn earworm, soybean looper, velvetbean caterpillar (*Lepidoptera: noctuidae*), and lesser cornstalk borer (*Lepidoptera: pyralidae*), J. Econ. Entomol. (2000) 93:613-622.*

* cited by examiner

*Primary Examiner* — Cathy Kingdon Worley
*Assistant Examiner* — Mykola Kovalenko
(74) *Attorney, Agent, or Firm* — Ronald S. Maciak; Faegre Baker Daniels LLP

(57) ABSTRACT

Soybean event 9582.814.19.1, wherein the event comprises genes encoding Cry1F, Cry1Ac (synpro), and PAT, affording insect resistance and herbicide tolerance to soybean crops containing the event, and enabling methods for crop protection and protection of stored products.

9 Claims, 2 Drawing Sheets

INSECT RESISTANT AND HERBICIDE TOLERANT SOYBEAN EVENT 9582.814.19.1

CROSS-REFERENCE TO RELATED APPLICATION

This application claims the benefits of U.S. Provisional Application No. 61/511,664, filed Jul. 26, 2011, and U.S. Provisional Application No. 61/521,798, filed Aug. 10, 2011, both of which are herein incorporated by reference in their entireties.

BACKGROUND OF INVENTION

The genes encoding Cry1F and Cry1Ac synpro (Cry1Ac) are capable of imparting insect resistance, e.g. resistance to lepidopteran insects, to transgenic plants; and the gene encoding PAT (phosphinothricin acetyltransferase) is capable of imparting tolerance to the herbicide phoshpinothricin (glufosinate) to transgenic plants. PAT has been successfully expressed in soybean for use both as a selectable marker in producing insect resistant transgenic crops, and to impart commercial levels of tolerance to the herbicide glufosinate in transgenic crops.

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event in order to determine whether progeny of a sexual cross contain a transgene or group of transgenes of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgenic event by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of soybean event 9582.814.19.1.

BRIEF SUMMARY OF THE INVENTION

The present invention relates to a new insect resistant and herbicide tolerant transgenic soybean transformation event, designated soybean event 9582.814.19.1, comprising cry1F, cry1Ac and pat, as described herein, inserted into a specific site within the genome of a soybean cell. Representative soybean seed has been deposited with American Type Culture Collection (ATCC) with the Accession No. identified in paragraph [0021]. The DNA of soybean plants containing this event includes the junction/flanking sequences described herein that characterize the location of the inserted DNA within the soybean genome. SEQ ID NO:1 and SEQ ID NO:2 are diagnostic for soybean event 9582.814.19.1. More particularly, sequences surrounding the junctions at bp 1400/1401, and bp 1536/1537 of SEQ ID NO:1, and bp 152/153 of SEQ ID NO:2 are diagnostic for soybean event 9582.814.19.1. Paragraph [00012] below describes examples of sequences comprising these junctions that are characteristic of DNA of soybeans containing soybean event 9582.814.19.1.

In one embodiment, the invention provides a soybean plant, or part thereof, that is resistant to *Pseudoplusia includens* (soybean looper) and that has a genome comprising one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof. In another embodiment, the invention provides seed of such plants.

In another embodiment, the invention provides a method of controlling insects that comprises exposing insects to insect resistant soybean plants, wherein the soybean plants have a genome that contains one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof; which are characteristic of the presence of soybean event 9582.814.19.1, to thereby control the insects. Presence of the cry1F v3 (cry1F) and cry1Ac synpro (cry1Ac) genes in soybean event 9582.814.19.1 imparts resistance to, for example, *Pseudoplusia includens* (soybean looper), *Anticarsia gemmatalis* (velvetbean caterpillar), *Epinotia aporema*, *Omoides indicatus*, *Rachiplusia nu*, *Spodoptera frugiperda*, *Spodoptera cosmoides*, *Spodoptera eridania*, *Heliothis virescens*, *Heliocoverpa zea*, *Spilosoma virginica* and *Elasmopalpus lignosellus*.

In another embodiment, the invention provides a method of controlling weeds in a soybean crop that comprises applying glufosinate herbicide to the soybean crop, said soybean crop comprising soybean plants that have a genome containing one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof, which are diagnostic for the presence of soybean event 9582.814.19.1. Presence of the pat v6 (pat) gene in soybean event 9582.814.19.1 imparts tolerance to glufosinate herbicide.

In another embodiment, the invention provides a method of detecting soybean event 9582.814.19.1 in a sample comprising soybean DNA, said method comprising:
(a) contacting said sample with
a first primer at least 10 bp in length that selectively binds to a flanking sequence within bp 1-1400 of SEQ ID NO:1 or the complement thereof, and a second primer at least 10 bp in length that selectively binds to an insert sequence within bp 1401-1836 of SEQ ID NO:1 or the complement thereof; and assaying for an amplicon generated between said primers; or
(b) contacting said sample with a first primer at least 10 bp in length that selectively binds to an insert sequence within bp 1-152 of SEQ ID NO:2 or the complement thereof, and a second primer at least 10 bp in length that selectively binds to flanking sequence within bp 153-1550 of SEQ ID NO:2 or the complement thereof; and
(c) assaying for an amplicon generated between said primers.

In another embodiment, the invention provides a method of detecting soybean event 9582.814.19.1 comprising:
(a) contacting said sample with a first primer that selectively binds to a flanking sequence selected from the group consisting of bp 1-1400 of SEQ ID NO:1 and bp 153-1550 of SEQ ID NO:2, and complements thereof; and a second primer that selectively binds to SEQ ID NO:3, or the complement thereof;
(b) subjecting said sample to polymerase chain reaction; and
(c) assaying for an amplicon generated between said primers.

In another embodiment the invention provides a method of breeding a soybean plant comprising: crossing a first plant with a second soybean plant to produce a third soybean plant, said first plant comprising DNA comprising one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof; and assaying said third soybean plant for presence of DNA comprising one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof.

In another embodiment the invention provides an isolated DNA molecule that is diagnostic for soybean event 9582.814.19.1. Such molecules include, in addition to SEQ ID NOS: 1 and 2, molecules at least 25 bp in length comprising bp 1400-1401 of SEQ ID NO:1 and at least 10 bp of SEQ ID NO:1 in each direction from the bp 1400/1401 junction; amplicons at least 25 bp in length comprising 152-153 of SEQ ID NO:2 and at least 10 bp of SEQ ID NO:2 in each direction from the bp 152/153 junction. Examples are bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof.

In another embodiment the invention provides a method of controlling pests in soybean grain, seed, or seed meal which comprises including soybean event 9582.814.19.1 in said grain, seed, or seed meal as demonstrated by said grain, seed, or seed meal comprising DNA comprising one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2, and complements thereof.

The invention also includes soybean plant cells and plant parts including, but are not limited to pollen, ovule, flowers, shoots, roots, and leaves, and nuclei of vegetative cells, pollen cells, seed and seed meal, and egg cells, that contain soybean event 9582.814.19.1.

In some embodiments, soybean event 9582.814.19.1 can be combined with other traits, including, for example, other herbicide tolerance gene(s) and/or insect-inhibitory proteins and transcription regulatory sequences (i.e. RNA interference, dsRNA, transcription factors, etc). The additional traits may be stacked into the plant genome via plant breeding, re-transformation of the transgenic plant containing soybean event 9582.814.19.1, or addition of new traits through targeted integration via homologous recombination.

Other embodiments include the excision of polynucleotide sequences which comprise soybean event 9582.814.19.1, including for example, the pat gene expression cassette. Upon excision of a polynucleotide sequence, the modified event may be re-targeted at a specific chromosomal site wherein additional polynucleotide sequences are stacked with soybean event 9582.814.19.1.

In one embodiment, the present invention encompasses a soybean chromosomal target site located on chromosome 02 between the flanking sequences set forth in SEQ ID NOS:1 and 2.

In one embodiment, the present invention encompasses a method of making a transgenic soybean plant comprising inserting a heterologous nucleic acid at a position on chromosome 02 between the genomic sequences set forth in SEQ ID NOS:1 and 2, i.e. between bp 1-1400 of SEQ ID NO:1 and bp 153-1550 of SEQ ID NO:2.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

The subject invention relates in part to the cloning and analysis of the DNA sequences of the border regions resulting from insertion of T-DNA from pDAB9582 in transgenic soybean lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify soybean lines comprising the event of the subject invention.

SEED DEPOSIT

As part of this disclosure at least 2500 seeds of a soybean line comprising soybean event 9582.814.19.1 were deposited with the American Type Culture Collection (ATCC), 10801 University Boulevard, Manassas, Va., 20110. The deposit, ATCC Patent Deposit Designation, PTA-12006, was received by the ATCC on Jul. 21, 2011. This deposit was made and will be maintained in accordance with and under the terms of the Budapest Treaty with respect to seed deposits for the purposes of patent procedure. This deposit was made and will be maintained in accordance with and under the terms of the Budapest Treaty with respect to seed deposits for the purposes of patent procedure.

BRIEF DESCRIPTION OF THE SEQUENCES

SEQ ID NO:1 is the 5' DNA flanking border sequence for soybean event 9582.814.19.1. Nucleotides 1-1400 are genomic sequence. Nucleotides 1401-1535 are a rearranged sequence from pDAB9582. Nucleotides 1536-1836 are insert sequence.

SEQ ID NO:2 is the 3' DNA flanking border sequence for soybean event 9582.814.19.1. Nucleotides 1-152 are insert sequence. Nucleotides 153-1550 are genomic sequence.

SEQ ID NO:3 is the DNA sequence of pDAB9582, which is annotated below in Table 1.

SEQ ID NO:4 is oligonucleotide primer 81419_FW3 for confirmation of 5' border genomic DNA.

SEQ ID NO:5 is oligonucleotide primer 81419_RV1 for confirmation of 3' border genomic DNA.

SEQ ID NO:6 is oligonucleotide primer 81419_RV2 for confirmation of 3' border genomic DNA.

SEQ ID NO:7 is oligonucleotide primer 81419_RV3 for confirmation of 3' border genomic DNA.

SEQ ID NO:8 is oligonucleotide primer 5'IREnd-01 for confirmation of 5' border genomic DNA.

SEQ ID NO:9 is oligonucleotide primer 5'IREnd-02 for confirmation of 5' border genomic DNA.

SEQ ID NO:10 is oligonucleotide primer AtUbi10RV1 for confirmation of 5' border genomic DNA.

SEQ ID NO:11 is oligonucleotide primer AtUbi10RV2 for confirmation of 5' border genomic DNA.

SEQ ID NO:12 is oligonucleotide primer 3'PATEnd05 for confirmation of 3' border genomic DNA.

SEQ ID NO:13 is oligonucleotide primer 3'PATEnd06 for confirmation of 3' border genomic DNA.

SEQ ID NO:14 is the confirmed sequence of soybean event 9582.814.19.1. Including the 5' genomic flanking sequence, pDAB9582 T-strand insert, and 3' genomic flanking sequence.

DETAILED DESCRIPTION OF THE INVENTION

Figure 1:
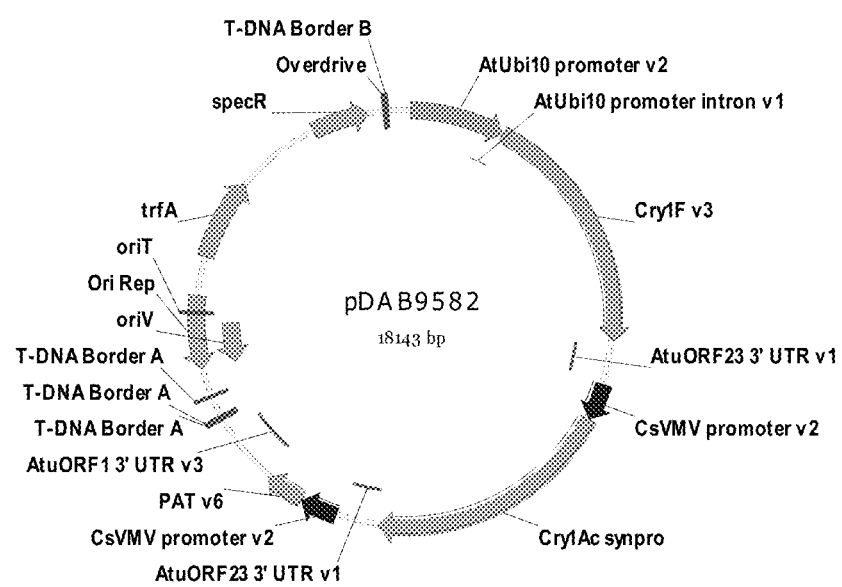
FIG. 1 is a plasmid Map of pDAB9582 containing the cry1F, cry1Ac and pat expression cassettes.

Both ends of the soybean event 9582.814.19.1 insertion have been sequenced and characterized. Event specific assays were developed. It has also been mapped onto the soybean genome (soybean chromosome 02). The event can be introgressed into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the biolistic transformation (i.e. gene gun), and silicon carbide mediated transformation (i.e. WHISKERS), it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises soybean event 9582.814.19.1.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The flanking/junction sequences are diagnostic for soybean event 9582.814.19.1. Based on these sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds available under the ATCC Deposit No. identified in paragraph [0021]. The subject invention also includes a herbicide-tolerant soybean plant grown from a seed deposited with the ATCC Deposit No. identified in paragraph [0021]. The subject invention further includes parts of said plant, such as leaves, tissue samples, seeds produced by said plant, pollen, and the like (wherein they comprise cry1F, cry1Ac, pat, and SEQ ID NOS: 1 and 2).

Still further, the subject invention includes descendant and/or progeny plants of plants grown from the deposited seed, preferably a herbicide-resistant soybean plant wherein said plant has a genome comprising a detectable wild-type junction sequence as described herein. As used herein, the term "soybean" means *Glycine max* and includes all varieties thereof that can be bred with a soybean plant.

This invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

An insect resistant/glufosinate-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to glufosinate; selfing the first progeny plant, thereby producing a plurality of second progeny plants; and then selecting from the second progeny plants a plant that is resistant to glufosinate. These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

Likewise an insect resistant/glufosinate-tolerant soybean plant of the subject invention can be transformed with additional transgenes using methods known in the art. Transformation techniques such as *Agrobacterium* transformation, the biolistic transformation (i.e. gene gun), and silicon carbide mediated transformation (i.e. WHISKERS), can be used to introduced additional trangene(s) into the genome of soybean event 9582.814.19.1. Selection and characterization of transgenic plants containing the newly inserted transgenes can be completed to identify plants which contain a stable integrant of the novel transgene in addition to cry1F, cry1Ac, pat genes of the subject invention.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The insect resistance and herbicide-tolerance traits can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the herbicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing an insect resistant/herbicide-tolerant soybean plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention and favorable varietal performance (e.g. yield). For example, the subject invention can be used to track the subject event through breeding cycles with plants comprising other desirable traits, such as agronomic traits, disease tolerance or resistance, nematode tolerance or resistance and maturity date. Plants comprising the subject event and the desired trait can be detected, identified, selected, and quickly used in further rounds of breeding, for example. The subject event/trait can also be combined through breeding, and tracked according to the subject invention, with further insect resistant trait(s) and/or with further herbicide tolerance traits. Embodiments of the latter are plants comprising the subject event combined with the aad-12 gene, which confers tolerance to 2,4-dichlorophenoxyacetic acid and pyridyloxyacetate herbicides, or with a gene encoding resistance to the herbicide dicamba.

Thus, the subject invention can be combined with, for example, traits encoding glyphosate resistance (e.g., resistant plant or bacterial EPSPS, GOX, GAT), glufosinate resistance (e.g., pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Additionally, soybean event 9582.814.19.1 can be combined with one or more additional input (e.g., insect resistance, pathogen resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1, herein incorporated by reference, describes the use of recombinases or integrases to mediate the introduction of a donor polynucleotide sequence into a chromosomal target. In addition, International Patent Application No. WO 2008/021207, herein incorporated by reference, describes zinc finger mediated-homologous recombination to integrate one or more donor polynucleotide sequences within specific locations of the genome. The use of recombinases such as FLP/FRT as described in U.S. Pat. No. 6,720,475, herein incorporated by reference, or CRE/LOX as described in U.S. Pat. No. 5,658,772, herein incorporated by reference, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other methods for site specific integration within plant cells are generally known and applicable (Kumar et al., *Trends in Plant Sci.* 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual outcrossing using conventional breeding methods.

In some embodiments of the present invention, it can be desirable to excise polynucleotide sequences from a transgenic event. For instance transgene excision as described in Provisional U.S. Patent Application No. 61/297,628, herein incorporated by reference, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 02 in the soybean genome that is excellent for insertion of heterologous nucleic acids. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

A preferred plant, or a seed, of the subject invention comprises in its genome operative cry1F v3, cry1Ac synpro and pat v6 nucleotide sequences, as identified herein, together with at least 20-500 or more contiguous flanking nucleotides on both sides of the insert, as identified herein. Unless indicated otherwise, reference to flanking sequences refers to those identified with respect to SEQ ID NOS: 1 and 2. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations.

"Commercial Utility" is defined as having good plant vigor and high fertility, such that the crop can be produced by farmers using conventional farming equipment, and the oil with the described components can be extracted from the seed using conventional crushing and extraction equipment "Agronomically elite" means that a line has desirable agronomic characteristics such as yield, maturity, disease resistance, and the like, in addition to the insect resistance and herbicide tolerance due to the subject event(s). Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), as indicated in the Table above. One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 800 to 1400 of SEQ ID NO:14 and/or base pairs 13,897 to 14,497 of SEQ ID NO:14 are within the scope of the subject invention. Insert primers can likewise be designed anywhere on the, but base pairs 1400 to 2000 of SEQ ID NO:14 and/or base pairs 13,297 to 13,896 of SEQ ID NO:14, and can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject 5' transgene/genomic insertion region junction sequence provided herein (between base pairs 800 to 1400 of SEQ ID NO:14), segments thereof, and complements of the exemplified sequences and any segments thereof. DNA sequences are provided that comprise the subject 3' transgene/genomic insertion region junction sequence provided herein (between base pairs 13,897 to 14,497 of SEQ ID NO:14), segments thereof, and complements of the exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising soybean event 9582.814.19.1 of the subject invention, wherein said method comprises the steps of: (a) sexually crossing a first parental soybean line (comprising an expression cassettes of the present invention, which confers glufosinate tolerance to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises the insect resistant and glufosinate tolerant trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with a second primer set (said second primer set, when used in a nucleic-acid amplification reaction with genomic DNA from soybean plants, produces a second amplicon comprising the native soybean genomic DNA homologous to the soybean genomic region); and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also comprises a soybean seed and/or a soybean plant comprising at least one non-soybean event 9582.814.19.1 insert in the general vicinity of this genomic location. One option is to substitute a different insert in place of the one from soybean event pDAB9582.814.19.1 exemplified herein. In these general regards, targeted homologous recombination, for example, can be used according to the subject invention. This type of technology is the subject of, for example, WO 03/080809 A2 and the corresponding published U.S. application (US 20030232410). Thus, the subject invention includes plants and plant cells comprising a heterologous insert (in place of or with multi-copies of the cry1F, cry1Ac, or pat genes), flanked by all or a recognizable part of the flanking sequences identified herein (bp 1-1400 of SEQ ID NO:1 and bp 153-1550 of SEQ ID NO:2). An additional copy (or additional copies) of a cry1F, cry1Ac, or pat could also be targeted for insertion in this/these manner(s).

All patents, patent applications, provisional applications, and publications referred to or cited herein are incorporated by reference in their entirety to the extent they are not inconsistent with the explicit teachings of this specification The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.
  bp base pair
  ° C. degrees Celsius
  DNA deoxyribonucleic acid
  EDTA ethylenediaminetetraacetic acid
  kb kilobase
  µg microgram
  µL microliter
  mL milliliter
  M molar mass
  PCR polymerase chain reaction
  PTU plant transcription unit
  SDS sodium dodecyl sulfate
  SSC a buffer solution containing a mixture of sodium chloride and sodium citrate, pH 7.0
  TBE a buffer solution containing a mixture of Tris base, boric acid and EDTA, pH 8.3

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLES

Example 1

Transformation and Selection of the Cry1F and Cry1Ac Soybean Event pDAB9582.814.19.1

Transgenic soybean (*Glycine max*) containing the soybean event pDAB9582.814.19.1 was generated through *Agrobacterium*-mediated transformation of soybean cotyledonary node explants. The disarmed *Agrobacterium* strain EHA101 (Hood et al., 1993), carrying the binary vector pDAB9582 (FIG. 1) containing the selectable marker, pat v6, and the genes of interest, cry1F v3 and cry1Ac synpro, within the T-strand DNA region, was used to initiate transformation. The DNA sequence for pDAB9582 is given in SEQ ID NO:3, which is annotated below in Table 1.

TABLE 1

Gene elements located on pDAB9582.

| bp (SEQ ID NO: 3) | Construct element | Reference |
|---|---|---|
| 272-1593 | AtUbi10 Promoter | Callis, et al., (1990) *J. Biol. Chem.*, 265: 12486-12493 |
| 1602-5048 | Cry1F | Referenced above |
| 5151-5607 | ORF23 3'UTR | U.S. Pat. No. 5,428,147 |
| 5671-6187 | CsVMV Promoter | Verdaguer et al., (1996) *Plant Mol. Biol.*, 31: 1129-1139 |
| 6197-9667 | Cry 1AC | Referenced above |
| 9701-10157 | ORF23 3'UTR | U.S. Pat. No. 5,428,147 |
| 10272-10788 | CsVMV Promoter | Verdaguer et al., (1996) *Plant Mol. Biol.*, 31: 1129-1139 |
| 10796-11347 | PAT | Wohlleben et al., (1988) *Gene* 70: 25-37 |
| 11450-12153 | ORF1 3'UTR | Huang et al., (1990) *J. Bacteriol.* 172: 1814-1822 |

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, soybean event pDAB9582.814.19.1, was generated from an independent transformed isolate. The $T_1$ plants were backcrossed and introgressed into elite varieties over subsequent generations. The event was selected based on its unique characteristics such as single insertion site, normal Mendelian segregation, stable expression, and a superior combination of efficacy, including herbicide tolerance and agronomic performance. The following examples contain the data which were used to characterize soybean event pDAB9582.814.19.1.

Example 2

Characterization of Protein Expression in Soybean Event pDAB9582.814.19.1

The biochemical properties of the recombinant Cry1F, Cry1Ac, and PAT proteins expressed in soybean event 9582.814.19.1 were characterized. Quantitative enzyme-linked immunosorbent assay (ELISA) is a biochemical assay known within the art that can be used to characterize the biochemical properties of the proteins and confirm expression of these proteins in soybean event 9582.814.19.1.

Example 2.1

Expression of the PAT, Cry1F, and Cry1Ac Protein in Plant Tissues

Samples of soybean tissues were isolated from the test plants and prepared for expression analysis. The PAT protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an PAT ELISA kit in a sandwich format. The kit was used following the manufacturer's suggested protocol (Envirologix, Portland, Me.). This assay measured the expressed PAT protein.

The Cry1F protein was extracted from soybean plant tissues with a phosphate buffered saline solution containing the detergent Tween-20 (PBST). The plant tissue was centrifuged; the aqueous supernatant was collected, diluted with appropriate buffer as necessary, and analyzed using an Cry1F ELISA kit in a sandwich format. The kit was used following the manufacturer's suggested protocol (Strategic Diagnostics Inc., Newark, Del.). This assay measured the expressed Cry1F protein.

The Cry1Ac protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an Cry1Ac ELISA kit in a sandwich format. The kit was used following the manufacturer's suggested protocol (Strategic Diagnostics Inc., Newark, Del.). This assay measured the Cry1Ac protein.

Detection analysis was performed to investigate the expression stability and inheritability both vertically (between generations) and horizontally (between lineages within a generation) in soybean event pDAB9582.814.19.1.

Example 2.2

Expression of the PAT, Cry1F, and Cry1Ac Protein in Plant Tissues

Levels of Cry1F, Cry1Ac and PAT proteins were determined in Soybean Event 9582.814.19.1. The soluble, extractable proteins were measured using a quantitative enzyme-linked immunosorbent assay (ELISA) method from soybean leaf tissue. From $T_2$ to $T_6$ generations Soybean Events 9582.814.19.1, expression was stable (not segregating) and consistent across all lineages. Table 2 lists the mean expression level of the transgenic proteins in soybean event 9582.814.19.1.

TABLE 2

Mean expression level of different transgenic proteins in soybean event pDAB9582.814.19.1.
Expression Level of Different Proteins (ng/cm²)

| Event | Cry1F | Cry1Ac | PAT |
|---|---|---|---|
| Soybean event pDAB9582.814.19.1 | 133 | 17.4 | 12 |

Example 3

Cloning and Characterization of DNA Sequence in the Insert and the Flanking Border Regions of Soybean Event pDAB9582.814.19.1

To characterize and describe the genomic insertion site, the sequence of the flanking genomic T-DNA border regions of soybean event pDAB9582.814.19.1 were determined. Genomic sequence of soybean event pDAB9582.814.19.1 was confirmed, comprising 1400 bp of 5' flanking border sequence (SEQ ID NO:1) and 1398 bp of 3' flanking border sequence (SEQ ID NO:2). PCR amplification based on the soybean event pDAB9582.814.19.1 border sequences validated that the border regions were of soybean origin and that the junction regions are unique sequences for soybean event pDAB9582.814.19.1. The junction regions could be used for event-specific identification of soybean event pDAB9582.814.19.1. In addition, the T-strand insertion site was characterized by amplifying a genomic fragment corresponding to the region of the identified flanking border sequences from the genome of untransformed soybean. Comparison of soybean event pDAB9582.814.19.1 with the untransformed genomic sequence revealed that a deletion of about 57 bp from the original locus resulted during the T-strand integration. Overall, the characterization of the insert and border sequence of soybean event pDAB9582.814.19.1 indicated that an intact copy of the T-strand from pDAB9582 was present in the soybean genome.

TABLE 3

List of primers and their sequences used in the confirmation of soybean genomic DNA in soybean event pDAB9582.814.19.1

| SEQ ID NO: | Primer Name | Size (bp) | Sequence (5' to 3') | Purpose |
|---|---|---|---|---|
| SEQ ID NO: 4 | 81419_FW3 | 30 | TTTCTCCTATCCGTC AAATAAATCTGCTCC | confirmation of 5' border genomic DNA, used with AtUbi10RV1 or RV2; with 5'IREnd-01 or 5'IREnd-02 |
| SEQ ID NO: 5 | 81419_RV1 | 27 | GGGTGATTTGGTGCC AAAAGTTATGTT | confirmation of 3' border genomic DNA, used with 3'PATEnd05 or 3'PATEnd06 |
| SEQ ID NO: 6 | 81419_RV2 | 24 | TGGAGGGTCATATCG CAAAAGACT | confirmation of 3' border genomic DNA, used with 3'PATEnd05 or 3'PATEnd06 |
| SEQ ID NO: 7 | 81419_RV3 | 24 | GTTCTGCGTCGTGGA GGGTCATAT | confirmation of 3' border genomic DNA, used with 3'PATEnd05 or 3'PATEnd06 |
| SEQ ID NO: 8 | 5'IREnd-01 | 29 | CGAGCTTTCTAATTT CAAACTATTCGGGC | confirmation of 5' border genomic DNA, used with 81419_FW3 |
| SEQ ID NO: 9 | 5'IREnd-02 | 30 | TCCTAGATCATCAGT TCATACAAACCTCCA | confirmation of 5' border genomic DNA, used with 81419_FW3 |
| SEQ ID NO: 10 | AtUbi10RV1 | 29 | CGGTCCTAGATCATC AGTTCATACAAACC | confirmation of 5' border genomic DNA, used with 81419_FW3 |
| SEQ ID NO: 11 | AtUbi10RV2 | 28 | CACTCGTGTTCAGTC CAATGACCAATAA | confirmation of 5' border genomic DNA, used with 81419_FW3 |
| SEQ ID NO: 12 | 3'PATEnd05 | 20 | GCTCCTCCAAGGCCA GTTAG | confirmation of 3' border genomic DNA, used with 81419_RV1, RV2 or RV3 |
| SEQ ID NO: 13 | 3'PATEnd06 | 20 | CCAGTTAGGCCAGTT ACCCA | confirmation of 3' border genomic DNA, used with 81419_RV1, RV2 or RV3 |

TABLE 4

Conditions for standard PCR amplification of the border regions and event-specific sequences in soybean event pDAB9582.814.19.1.

| Target Sequence | Primer Set | PCR Mixture | Pre-denature (° C./min) | Denature (° C./sec.) | Extension (° C./min:sec) | Final Extension (° C./min) |
|---|---|---|---|---|---|---|
| 5' border | 81419_FW3/ AtUbi10RV1 | D | 95/3 | 98/10 | 68/4:00 32 cycles | 72/10 |
| 5' border | 81419_FW3/ 5'IREnd-01 | D | 95/3 | 98/10 | 68/4:00 32 cycles | 72/10 |
| 3' border | 3'PATEnd05/ 81419_RV2 | D | 95/3 | 98/10 | 68/4:00 35 cycles | 72/10 |
| 3' border | 3'PATEnd05/ 81419_RV3 | D | 95/3 | 98/10 | 68/4:00 35 cycles | 72/10 |
| 3' border | 3'PATEnd06/ 81419_RV2 | D | 95/3 | 98/10 | 68/4:00 35 cycles | 72/10 |
| 3'border | 3'PATEnd06/ 81419_RV3 | D | 95/3 | 98/10 | 68/4:00 32 cycles | 72/10 |
| Across the insert locus | 81419_FW3/ 81419_RV3 | D | 95/3 | 98/10 | 68/4:00 32 cycles | 72/10 |

TABLE 5

PCR mixture for standard PCR amplification of the border regions and event specific sequences in soybean event pDAB9582.814.19.1.

| Reagent | 1 x reaction (μL) | Reagent | 1 x reaction (μL) |
|---|---|---|---|
| PCR Mixture A | | PCR Mixture B | |
| H20 | 0.8 | H20 | 14.6 |
| ACCPRIME PFX SUPERMIX | 20 | 10X LA TAQ BUFFER | 2 |
| — | — | MgCl2 (25 mM) | 0.6 |
| — | — | dNTP (2.5 uM) | 1.6 |
| 10 uM primer | 0.2 | 10 uM primer | 0.1 |
| gDNA digestion | 1 | gDNA digestion | 1 |
| — | — | LA TAQ (5U/ul) | 0.1 |
| rxn vol: | 22 | rxn vol: | 20 |
| PCR Mixture C | | PCR Mixture D | |
| H20 | 28 | H20 | 11.6 |
| 10X PCR buffer II (Mg-plus) | 5 | 10X PCR buffer II (Mg-plus) | 2 |
| $MgCl_2$[25 mM] | 1.5 | $MgCl_2$ [25 mM] | 0.6 |
| dNTP [2.5 mM] | 8 | dNTP [2.5 mM] | 3.2 |
| Adaptor PCR primer (10 μM) | 1 | primer1 (10 μM) | 0.4 |
| GOI nested primer (10 μM) | 1 | primer2 (10 μM) | 0.4 |
| DNA binded Beads | 5 | DNA Template | 0.2 |
| LA TAQ (5U/ul) | 0.5 | LA TAQ (5U/ul) | 1.6 |
| rxn vol: | 50 | rxn vol: | 20 |

Example 3.1

Confirmation of Soybean Genomic Sequences

Figure 2:
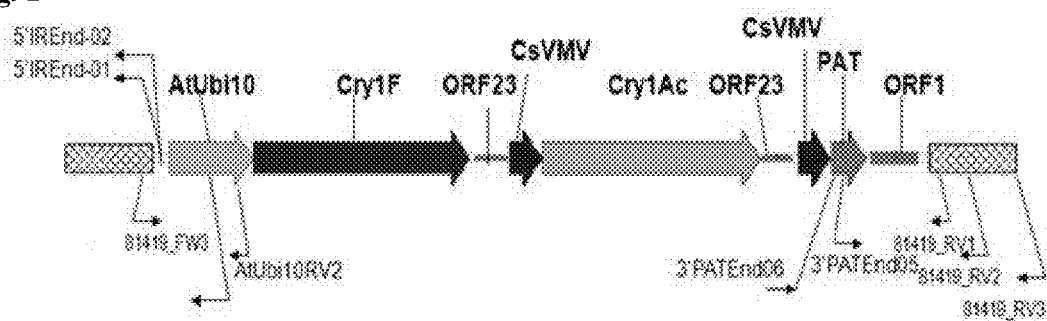
FIG. 2 depicts the primer locations for confirming the 5' and 3' border sequence of the soybean event pDAB9582.814.19.1.

The 5' and 3' flanking borders aligned to a *Glycine max* whole genome shotgun sequence from chromosome 02, indicating that the transgene of soybean event pDAB9582.814.19.1 was inserted in soybean genome chromosome 02. To confirm the insertion site of soybean event pDAB9582.814.19.1 from the soybean genome, PCR was carried out with different pairs of primers (FIG. 2, Table 3, Table 4, and Table 5). Genomic DNA from soybean event pDAB9582.814.19.1 and other transgenic or non-transgenic soybean lines was used as a template. To confirm that the 5' border sequences are correct a primer designed to bind to the At Ubi10 promoter gene element, for example AtUbi10RV1, and a primer designed to bind to the cloned 5' end border on soybean genome chromosome 02, primer designated 81419_FW3, were used for amplifying the DNA segment that spans the At Ubi10 promoter gene element to 5' end border sequence. Similarly, for confirmation of the cloned 3' border sequence a pat specific primer, for example 3'PATEnd05, and three primers designed according to the cloned 3' end border sequence, designated 81419_RV1, 81419_RV2 and 81419_RV3, were used for amplifying DNA segments that span the pat gene to 3' border sequence. DNA fragments with expected sizes were amplified only from the genomic DNA of soybean event pDAB9582.814.19.1 with each primer pair, but not from DNA samples from other transgenic soybean lines or the non-transgenic control. The results indicate that the cloned 5' and 3' border sequences are the flanking border sequences of the T-strand insert for soybean event pDAB9582.814.19.1

Figure 3:
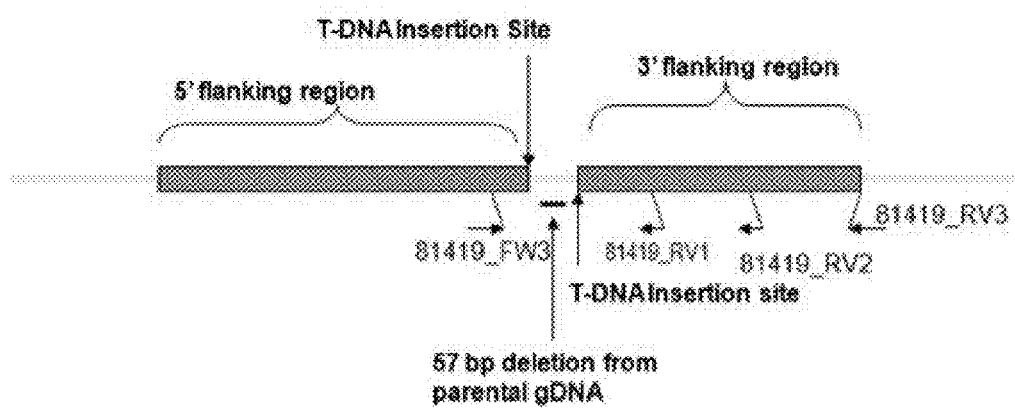
FIG. 3 depicts the genomic sequence arrangement in soybean event pDAB9582.814.19.1

To further confirm the DNA insertion in the soybean genome, a PCR amplification spanning the soybean border sequences was completed on genomic DNA which did not contain the T-strand insert for soybean event pDAB9582.814.19.1. Primer 81419_FW3, designed according to the 5' end border sequence, and one primer 81419-RV3, designed for the 3' end border sequence, were used to amplify DNA segments which contained the locus where the pDAB9582 T-strand integrated. As expected, PCR amplification completed with the primer pair of 81419_FW3 and 81419_RV3 produced an approximately a 1.5 kb DNA fragment from all the other soybean control lines but not pDAB9582.814.19.1. Aligning the identified 5' and 3' border sequences of soybean event pDAB9582.814.19.1 with a *Glycine max* whole genome shotgun sequence from chromosome 02 revealed about 57 bp deletion from the original locus. (FIG. 3). These results demonstrated that the transgene of soybean event pDAB8294 was inserted into the site of soybean genome chromosome 02.

Example 4

Soybean Event pDAB9582.814.19.1 Characterization via Southern Blot

Southern blot analysis was used to establish the integration pattern of soybean event pDAB9582.814.19.1. These experiments generated data which demonstrated the integration and integrity of the cry1Ac and cry1F transgenes within the soybean genome. Soybean event pDAB9582.814.19.1 was characterized as a full length, simple integration event containing a single copy of the cry1Ac and cry1F plant transcription unit (PTU) from plasmid pDAB9582.

Southern blot data suggested that a T-strand fragment inserted into the genome of soybean event pDAB9582.814.19.1. Detailed Southern blot analysis was conducted using probes specific to the cry1Ac and cry1F gene, contained in the T-strand integration region of pDAB9582.814.19.1, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the cry1Ac and cry1F PTU.

Example 4.1

Soybean Leaf Sample Collection and Genomic DNA (gDNA) Isolation

Genomic DNA was extracted from leaf tissue harvested from individual soybean plants containing soybean event pDAB9582.814.19.1. In addition, gDNA was isolated from a conventional soybean plant, Maverick, which contains the genetic background that is representative of the substance line, absent the cry1Ac and cry1F genes. Individual genomic DNA was extracted from lyophilized leaf tissue following the standard CTAB method (Sambrook et al (1989)). Following extraction, the DNA was quantified spectrofluorometrically using PICO GREEN reagent (Invitrogen, Carlsbad, Calif.). The DNA was then visualized on an agarose gel to confirm values from the PICO GREEN analysis and to determine the DNA quality.

Example 4.2

DNA Digestion and Separation

For Southern blot molecular characterization of soybean event pDAB9582.814.19.1, ten micrograms (10 µg) of genomic DNA was digested. Genomic DNA from the soybean event pDAB9582.814.19.1 and non-transgenic soybean line Maverick was digested by adding approximately five units of selected restriction enzyme per µg of DNA and the corresponding reaction buffer to each DNA sample. Each sample was incubated at approximately 37° C. overnight. The restriction enzymes AseI, HindIII, NsiI, and NdeI were used individually for the single digests (New England Biolabs, Ipswich, Mass.). The restriction enzymes NotI and ApaLI were used together for a double digestion (New England Biolabs, Ipswich, Mass.). In addition, a positive hybridization control sample was prepared by combining plasmid DNA, pDAB9582 with genomic DNA from the non-transgenic soybean variety, Maverick. The plasmid DNA/genomic DNA cocktail was digested using the same procedures and restriction enzyme as the test samples.

After the digestions were incubated overnight, 25 µL QUICK-PRECIP PLUS SOLUTION (Edge Biosystems, Gaithersburg, Md.) was added and the digested DNA samples were precipitated with isopropanol. The precipitated DNA pellet was resuspended in 15 µL of 1× loading buffer (0.01% bromophenol blue, 10.0 mM EDTA, 10.0% glycerol, 1.0 mM Tris pH 7.5). The DNA samples and molecular size markers were then electrophoresed through 0.85% agarose gels with 0.4× TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light.

Example 4.3

Southern Transfer and Membrane Treatment

Southern blot analysis was performed essentially as described by Memelink, et al. (1994). Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer the DNA was bound to the membrane by UV crosslinking following by briefly washing membrane with a 2×SSC solution. This process produced Southern blot membranes ready for hybridization.

Example 4.4

DNA Probe Labeling and Hybridization

The DNA fragments bound to the nylon membrane were detected using a labeled probe (Table 6). Probes were generated by a PCR-based incorporation of a digoxigenin (DIG) labeled nucleotide, [DIG-11]-dUTP, into the DNA fragment amplified from plasmid pDAB9582 using primers specific to gene elements. Generation of DNA probes by PCR synthesis was carried out using a PCR DIG Probe Synthesis Kit (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG EASY HYB SOLUTION (Roche Diagnostics, Indianapolis, Ind.). Briefly, nylon membrane blots containing fixed DNA were briefly washed with 2×SSC and pre-hybridized with 20-25 mL of pre-warmed DIG EASY HYB SOLUTION in hybridization bottles at approximately 45-55° C. for about 2 hours in a hybridization oven. The pre-hybridization solution was then decanted and replaced with ~15 mL of pre-warmed DIG EASY HYB SOLUTION containing a desired amount of specific probes denatured by boiling in a water bath for approximately five minutes. The hybridization step was then conducted at approximately 45-55° C. overnight in the hybridization oven.

At the end of the probe hybridization, DIG EASY HYB SOLUTIONS containing the probes were decanted into clean tubes and stored at approximately −20° C. These probes could be reused up to two times according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Maleic acid buffer from the DIG WASH AND BLOCK BUFFER SET (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-STAR CHEMILUMINESCENT NUCLEIC ACID DETECTION SYSTEM (Roche Diagnostics, Indianapolis, Ind.) following the manufacturer's recommendation. Blots were exposed to chemiluminescent film for one or more time points to detect hybridizing fragments and to visualize molecular size standards. Films were developed with an ALL-PRO 100 PLUS film developer (Konica Minolta, Osaka, Japan) and images were scanned. The number and sizes of detected bands were documented for each probe. DIG-LABELED DNA MOLECULAR WEIGHT MARKER II (DIG MWM II) and DIG-LABELED DNA MOLECULAR WEIGHT MARKER VII (DIG MWM VII), visible after DIG detection as described, were used to determine hybridizing fragment size on the Southern blots.

TABLE 6

Location and length of probes used in Southern analysis.

| Probe Name | Genetic Element | Length (bp) |
| --- | --- | --- |
| Cry1Ac | cry1Ac | 1720 |
| Cry1F | cry1F | 1746 |
| specR | Spectinomycin resistance gene | 750 |
| OriRep | Ori Rep | 852 |
| trfA | Replication initiation protein trfA | 1119 |

Example 4.5

Southern Blot Results

Expected and observed fragment sizes with a particular digest and probe, based on the known restriction enzyme sites of the cry1Ac and cry1F PTU, are given in Table 7. Two types of fragments were identified from these digests and hybridizations: internal fragments where known enzyme sites flank the probe region and are completely contained within the insertion region of the cry1Ac and cry1F PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of soybean containing soybean event pDAB9582.814.19.1 produced data which suggested that a low copy, intact cry1Ac and cry1F PTU from plasmid pDAB9582 was inserted into the soybean genome of soybean event pDAB9582.814.19.1.

TABLE 7

Predicted and observed hybridizing fragments in Southern blot analysis.

| DNA Probe | Restriction Enzymes | Samples | Expected Fragment Sizes (bp)[1] | Observed Fragment Size (bp)[2] |
| --- | --- | --- | --- | --- |
| Cry1Ac | AseI | pDAB9582 | 13476 | >14000 |
| | | Maverick | none | none |
| | | Soybean Event pDAB9582.814.19.1 | >7286 | ~7400 |
| | NsiI | pDAB9582 | 15326 | >15000 |
| | | Maverick | none | none |
| | | Soybean Event pDAB9582.814.19.1 | >9479 | >10000 |
| | Not I + ApaLI | pDAB9582 | 4550 | ~4500 |
| | | Maverick | none | none |
| | | Soybean Event pDAB9582.814.19.1 | 4550 | ~4500 |
| Cry1F | NdeI | pDAB9582 | 8071 | ~8000 |
| | | Maverick | none | none |
| | | Soybean Event pDAB9582.814.19.1 | 5569 | ~7500 |
| | NsiI | pDAB9582 | 11044 | 11000 |
| | | Maverick | none | none |
| | | Soybean Event pDAB9582.814.19.1 | >9479 | >10000 |
| | Hind III | pDAB9582 | 7732 | ~7700 |
| | | Maverick | none | none |
| | | Soybean Event pDAB9582.814.19.1 | 7732 | ~7700 |
| SpecR | NsiI | pDAB9582 | 15320 | ~15000 |
| | | Maverick | none | none |
| | | Soybean Event pDAB9582.814.19.1 | none | none |
| trfA | NsiI | pDAB9582 | 15320 | ~15000 |
| | | Maverick | none | none |
| | | Soybean Event pDAB9582.814.19.1 | none | none |
| oriREP | NdeI | pDAB9582 | 5239 | ~5000 |
| | | Maverick | none | none |
| | | Soybean Event pDAB9582.814.19.1 | none | none |

[1]Expected fragment sizes are based on the plasmid map of pDAB9582.
[2]Observed fragment sizes are considered approximately from these analyses and are based on the indicated sizes of the DIG-LABELED DNA MOLECULAR WEIGHT MARKER II and MARK VII fragments.

The restriction enzymes AseI and NsiI bind and cleave unique restriction sites in plasmid pDAB9582. Subsequently, these enzymes were selected to characterize the cry1Ac gene insert in soybean event pDAB9582.814.19.1. Border fragments of >7286 bp or >9479 bp were predicted to hybridize with the probe following AseI and NsiI digests, respectively (Table 7). Single cry1Ac hybridization bands of about 7400 and >10000 bp were observed when AseI and NsiI digests were used, respectively. The hybridization of the probe to bands of this size suggests the presence of a single site of insertion for the cry1Ac gene in the soybean genome of soybean event pDAB9582.814.19.1. Restriction enzymes NotI and ApaLI were selected to perform a double digestion and to release a fragment which contains the cry1Ac plant transcription unit (PTU; promoter/gene/terminator) (Table 7). The predicted 4550 bp fragments were observed with the probe following NotI and ApaLI double digestion. Results obtained with the enzyme digestion of the pDAB9582.814.19.1 samples followed by probe hybridization indicated that an intact cry1Ac PTU from plasmid pDAB9582 was inserted into the soybean genome of soybean event pDAB9582.814.19.1.

The restriction enzymes NdeI and NsiI bind and cleave restriction sites in plasmid pDAB9582. Subsequently, these enzymes were selected to characterize the cry1F gene insert in soybean event pDAB9582.814.19.1. Border fragments of >5569 bp and >9479 were predicted to hybridize with the probe following the NdeI and NsiI digests, respectively (Table 7). Single cry1F hybridization bands of ~7500 bp and >10000 bp were observed when NdeI and NsiI were used, respectively. The hybridization of the probe to bands of this size suggests the presence of a single site of insertion for the cry1F gene in the soybean genome of soybean event pDAB9582.814.19.1. Restriction enzyme, HindIII, was selected to release a fragment which contains the cry1F plant transcription unit (PTU; promoter/gene/terminator) (Table 7). The predicted 7732 bp fragment was observed with the probe following the HindIII digestions. Results obtained with the enzyme digestion of the pDAB9582.814.19.1 samples followed by probe hybridization indicated that an intact cry1F PTU from plasmid pDAB9582 was inserted into the soybean genome of soybean event pDAB9582.814.19.1.

Example 4.6

Absence of Backbone Sequences

Southern blot analysis was also conducted to verify the absence of the spectinomycin resistance gene (specR), Ori Rep element and replication initiation protein trfA (trf A element) in soybean event pDAB9582.814.19.1. No specific hybridization to spectinomycin resistance, Ori Rep element or trf A element is expected when appropriate positive (pDAB9582 added to Maverick genomic DNA) and negative (Maverick genomic DNA) controls are included for Southern analysis. Following the NsiI digestion and hybridization with the specR specific probe, one expected size band of 15320 bp was observed in the positive control sample (pDAB9582 added to Maverick genomic DNA). The specR probe did not hybridize to samples of the negative control and soybean event pDAB9582.814.19.1. Similarly, one expected size band of 15320 bp was detected in the positive control sample (pDAB9582 plus maverick) but absent from the samples of the negative control and soybean event pDAB9582.814.19.1 after NsiI digestion and hybridization with trfA probe. Another expected size band of 5329 bp was detected in the positive control sample (pDAB9582 added to Maverick genomic DNA) but absent from the samples of the negative control and soybean event pDAB9582.814.19.1 after NdeI digestion and hybridization with OriRep specific probe. These data indicate the absence of spectinomycin resistance gene, Ori Rep element and replication initiation protein trfA in soybean event pDAB9582.814.19.1.

Example 5

Agronomic and Yield Field Trial and Herbicide Tolerance

To test the agronomic characteristics and efficacy of soybean event pDAB9582.814.19.1 the event was planted in an efficacy trial at Santa Isabel, Puerto Rico in October 2010 and February 2011. The cultivar Maverick, which was originally transformed to produce event pDAB9582.814.19.1, was planted in each nursery and included as a control in the experiments. Seed for the T3 nursery was derived from single plant selections at the T2 stage and seed for the T4 nursery was derived from single plant selections at the T3 stage. Four lineages of the event were tested each generation. Each lineage was planted in a plot which was 4 rows wide and 7.5 feet long. The spacing between rows was 30 inches. Plots were grown under lights for approximately 2.5 weeks to compensate for the short day length in Puerto Rico. Each nursery was sprayed with glufosinate at a rate of 411 g ae/ha. One plot of the control plants, Maverick, was sprayed with the same rate of glufosinate and a second plot was non-sprayed and used as control comparison for the event.

Data was collected on emergence, general appearance, vigor, height, lodging, and maturity. Herbicide tolerance was assessed by visually looking for chlorosis, leaf necrosis and plant death (Table 8).

For comparisons of soybean event pDAB9582.814.19.1 with Maverick, only data from the unsprayed block of Maverick were used. For comparison of the sprayed and non-sprayed treatments, data from the soybean event pDAB9582.814.19.1 block sprayed with a given treatment were compared with data from the Maverick control non-sprayed block. Soybean event pDAB9582.814.19.1 showed tolerance to the glufosinate herbicide application. In contrast, none of the Maverick plants were tolerant to the herbicide treatments.

TABLE 8

Comparison of soybean event pDAB9582.814.19.1 to Maverick. Values are averages from T3 and T4 nurseries. Each nursery of soybean event pDAB9582.814.19.1 was sprayed with glufosinate at the V3 stage at a rate of 411 g ae/ha.

| Event | Emergence (%) | Appearance (1 = poor to 9 = good) | Vigor (1 = poor to 9 = good) | Height (cm) | Lodging (%) | Maturity (day) |
|---|---|---|---|---|---|---|
| pDAB9582.814.19.1 | 90 | 8 | 8 | 69 | 1 | 91 |
| Maverick | 82 | 8 | 8 | 64 | 1 | 91 |

Example 6

Characterization of Insecticidal Activity for Soybean Event 9582.814.19.1

Field and greenhouse evaluations were conducted to characterize the activity of Cry1Ac and Cry1F in soybean event pDAB9582.814.19.1 against lab reared soybean pests including *Anticarsia gemmatalis* (velvetbean caterpillar), *Pseudoplusia includens* (soybean looper) and *Spodoptera frugiperda* (fall armyworm). Soybean event pDAB9582.814.19.1 was compared against non-transformed soybean variety Maverick, to determine the level of plant protection provided by the Cry1F and Cry1Ac proteins.

Greenhouse trials were conducted on approximately four week old plants. Fifteen plants were used to evaluate the soybean event pDAB9582.814.19.1 and the Maverick control. For each insect species tested (*Anticarsia gemmatalis, Pseudoplusia includes*, and *Spodoptera frugiperda*) 3 leaf punches were made from each plant for a total of 45 leaf discs/plant/insect species. The 1.4 cm diameter (or 1.54 $cm^2$) leaf punches were placed in a test arena on top of 2% water agar, infested with one neonate larvae and sealed with a perforated plastic lid. Mortality and leaf consumption were rated 4 days after infestation. Larvae that were not responsive to gentle probing were considered dead. Leaf damage was assessed by visually scoring the percentage of leaf punch consumed by the insect.

Field evaluations were conducted by collecting leaf samples from seed increase nursery plots in Santa Isabel, Puerto Rico and sending these leaves to Indianapolis, Ind. for testing. The nursery plot for soybean event pDAB9582.814.19.1 was planted in February 2011 and consisted of approximately 180 plants arranged in four rows. Each row was 2.3 m long and spaced 76.2 cm apart; individual plants were spaced 5.1 cm apart within each row. In March 2011, one fully-expanded, mainstem trifoliate leaf, located approximately four nodes below the meristem, was excised from 10 soybean event pDAB9582.814.19.1 plants and 10 ‘Maverick’ plants. The leaves were placed in labeled plastic bags, (one per bag) and sealed. The bagged leaves were packed and transferred to the laboratory. In the laboratory, one or two 3.33 cm (1.31 in) diameter leaf discs were punched from each trifoliate leaf to provide a total of 16 leaf discs. Each leaf disc was placed a in test arena on top of 2% agar, infested with one neonate *S. frugiperda* larva, and sealed with a perforated plastic lid. The leaf discs were held in a controlled environment chamber for 7 days, at which time mortality and leaf consumption were rated. Larvae not responsive to gentle probing were considered dead. Leaf damage was assessed by visually scoring the percentage of leaf punch consumed by the insect.

The results obtained from these replicated experiments indicated the soybean event pDAB9582.814.19.1 sustained significantly lower damage than the Maverick control plants for all insects tested. Thus, the soybean event pDAB9582.814.19.1 has insecticidal activity over this broad host range.

Example 7

Sequence of Soybean Event pDAB9582.814.19.1

SEQ ID NO:14 provides the sequence of soybean event pDAB9582.814.19.1. This sequence contains the 5' genomic flanking sequence, the T-strand insert of pDAB9582 and 3' genomic flanking sequences. With respect to SEQ ID NO:14, residues 1-1400 are 5' genomic flanking sequence, residues 1401-1536 are residues of a rearrangement from the pDAB9582 plasmid and 1537-13896 are residues of the pDAB9582 T-strand insert, and residues 13897-15294 are 3' flanking sequence. The junction sequence or transition with respect to the 5' end of the insert thus occurs at residues 1400-1401 of SEQ ID NO:14. The junction sequence or transition with respect to the 3' end of the insert thus occurs at residues 13896-13897 of SEQ ID NO:14.

It should be noted that progeny from soybean event pDAB9582.814.19.1 may have sequences which slightly deviate from SEQ ID NO:14. During the introgression and breeding process of introducing soybean event pDAB9582.814.19.1 into the genome of plant cells, it is not uncommon for some deletions or other alterations of the insert to occur. Moreover, errors in PCR amplification can occur which might result in minor sequencing errors. For example, flanking sequences listed herein were determined by generating amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention. Thus, the relevant segment of the plasmid sequence provided herein might comprise some minor variations. Thus, a plant comprising a polynucleotide having some range of identity with the subject insert sequence is within the scope of the subject invention. Identity to the sequence of SEQ ID NO:14 can be a polynucleotide sequence having at least 90%, 91%, 92%, 93%, 94%, 95%, 96%, 97%, 98%, 99%, or 100% sequence identity with a sequence exemplified or described herein. Thus, some differences between SEQ ID NO:14 and soybean event pDAB9582.814.19.1 progeny plants may be identified and are within scope of the present invention.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A method of controlling insects, said method comprising exposing insects to insect resistant soybean plants, said soybean plants comprising SEQ ID NO: 14, wherein said insects are selected from the group consisting of: *Pseudoplusia includens* (soybean looper), *Anticarsia gemmatalis* (velvet bean caterpillar) and *Spodoptera frugiperda* (fall armyworm).

2. The method of claim 1 wherein said insects are *Pseudoplusia includens* (soybean looper).

3. The method of claim 1 wherein said insects are *Anticarsia gemmatalis* (velvet bean caterpillar.

4. The method of claim 1 wherein said insects are *Spodoptera frugiperda* (fall armyworm).

5. A method of controlling weeds in a soybean crop, said method comprising applying glufosinate herbicide to the soybean crop, said soybean crop comprising soybean plants comprising SEQ ID NO:14.

6. A method of breeding a soybean plant, said method comprising: crossing a first plant with a second soybean plant to produce a third soybean plant, said first plant comprising DNA comprising SEQ ID NO:14; and assaying said third soybean plant for the presence of SEQ ID NO:14.

7. A soybean plant, wherein representative seed of said soybean plant has been deposited with the American Type Culture Collection under Accession No. PTA-12006.

8. A seed or a part of the plant of claim 7, wherein said seed or part comprises SEQ ID NO:14.

9. A soybean plant, or part thereof, comprising the DNA sequence of SEQ ID NO: 14.

* * * * *

UNITED STATES PATENT AND TRADEMARK OFFICE
CERTIFICATE OF CORRECTION

PATENT NO.         : 8,680,363 B2                                                Page 1 of 1
APPLICATION NO.    : 13/559177
DATED              : March 25, 2014
INVENTOR(S)        : Nathan Bard et al.

It is certified that error appears in the above-identified patent and that said Letters Patent is hereby corrected as shown below:

In The Claims

Column 65, Line 2 should read as follows:

sia gemmatalis (velvet bean caterpillar).

Signed and Sealed this
Sixth Day of January, 2015

Michelle K. Lee
*Deputy Director of the United States Patent and Trademark Office*

SEQUENCE LISTING

```
<160> NUMBER OF SEQ ID NOS: 14

<210> SEQ ID NO 1
<211> LENGTH: 1836
```

```
<212> TYPE: DNA
<213> ORGANISM: Glycine max

<400> SEQUENCE: 1
ttaacaatga ccaagattta tgctatatag aagacttgga gggcttaagg ctatgatata      60
ttatggatga tatggttctg atttgtgtag tttcgaagga tcaaatcaac catttgttgg     120
tacaatggga agaaaaaatg ttttcatcat tccactctat tgaaaaagat ccaacaattg     180
taacaccccg acgaatcaca ccggaaagag aagaatccaa agattgtgta ggtatgagac     240
tgtatagttg atgaaaactt aaaaaaatta attggtacta cttataccaa caagatgcat     300 atattttcg atagcctatc acataagaac ttcatagtta agggtgctta acttggagta     360
gttatgaaat gagtgacctt ttaaaataat tattgtctta ggttattgta tgaaaataaa     420
aaataataat aaatatacat aaaaaataat aattttataa aattaacctt atattatcat     480
taatttattt ttagatttg ttattcatta ttaatatatg aggtataaat gaaaatata     540 attaatgtca cattaaaaaa ttaaaatgat aattattttg aaacaaatta tttatttta     600 tacgacaatt ataatagaaa tttgagagta aaaaaaaatt gaaaattcat aaaatatatg     660
aatatattca tttctcctat ccgtcaaata aatctgctcc ataatttatc taagcattgg     720
tcttgtagtt cagagtaata aaattttagc aattattagt tagtacagat acatttaaag     780
aaataatata tttagcaac tagaagttta taaaagttt taaattataa agacttatat     840
ataaatttag taaaactaga tggatgtccc aagtaattt tatataacta ttctcgtaca     900
acattaatga aaatcttgtt tctattattt atatgtatat tattattta ttttggaaca     960 atatgggatt aaaaactctt ataaattaaa tcttagaata agttttccta acatgttttt    1020
tttatggatg ttttcctaac atgtttggtt atcttagttt tgctttaatt ttgtcggatt    1080 attttggac tttattaggt aattttgata aaacttttag ttgatgttag tagtttactc    1140
ttacataatg atttgatatt gaatgtgtat aattggaagg caataaatga agatcaagcg    1200
tacaagagtt cgccaatcaa gaggatttga agagagtaaa atattatgcg aagtcccatg    1260
tgaagaaaat ccaaccattg gaataaaaaa taaagttttt tctttggaat tgctaatgct    1320
acagcactta ttggtacttg tcctaaaaat gaaactctag ctatatttag cacttgatat    1380
tcatgaatca aacttctcta tgaaataacc gcggtgcgca tcggtgcctg ttgatcccgc    1440
gcaagttggg atcttgaagc aagttccgct catcactaag tcgcttagca tgtttgacct    1500
tctcggacaa ctccttcttc tctttaattg atcaacagtc agcatcatca caccaaaagt    1560
taggcccgaa tagtttgaaa ttagaaagct cgcaattgag gtctacaggc caaattcgct    1620
cttagccgta caatattact caccggatcc taaccggtgt gatcatgggc cgcgattaaa    1680
aatctcaatt atatttggtc taatttagtt tggtattgag taaaacaaat tcggcgccat    1740
gcccgggcaa gcggccgcac aagtttgtac aaaaaagcag ctccgcggt gactgactga    1800 aaagcttgtc gacctgcagg tcaacggatc aggata                             1836

<210> SEQ ID NO 2
<211> LENGTH: 1550
<212> TYPE: DNA
<213> ORGANISM: Glycine max

<400> SEQUENCE: 2
gcacatagac acacacatca tctcattgat gcttggtaat aattgtcatt agattgtttt      60
tatgcataga tgcactcgaa atcagccaat tttagacaag tatcaacgg atgtgacttc     120 agtacattaa aaacgtccgc aatatgatat tcattaattt tatattatct aaaagagtta     180
```

```
aaagagaaaa aagaaatatg acaatttttt tctttcacat cttctaacct aaaagtatga    240
ctctatggag gctaagttta gaaaagata cggatctagg gtgtggaaac atcaatggtc     300
aactcctttt atatttcaat caattgggtt ttgctttatc tttacatttt ctccttttat    360
tttccacgtc tattcaaatc tacttgttag cgggtgatta ctctttttc ttttatagat     420 gccaattatt tctctcctat gtattaaatt agagtatatt gtcttgaaag tgacttagta    480
ttttagttta tagtctctta aagaacgaca ccttttattc ttaactctct ttatcaagtt    540
ttaatttaaa attattttaa attaagtatg catacatatc ttaatatttt tcttaattat    600
ttttaaattc cctaaattta atgttttcat acaatgtaag agatatacat attaattata    660
tttaaagata aaacttactt tcctgcaata aaataaagaa aaggacagtc atacaattat    720
ataattaatc cagaatattt atagctttta aacatttatt ttctatcaat taagtaataa    780
ctttaaataa aattaagagt actttttat actccaaaga atttatttat tttcaacaaa     840
atcgtctgac tgtttcaatt gatcattatc agcctagcat aacctaaatt tcattttcaa    900
acataacttt tggcaccaaa tcacccggca ttgcaaaaaa gtcttttgcg atatgaccct    960
ccacgacgca gaaccactgt tattcattac catcactttt aatcctaatt tcccatacac    1020 ttacccttc catgacatct tcaaagcctt tattttgctt ttcttgttta agctgtttta    1080
acctaatttc atgcatataa acaaagagta aagcaaaggc aaatatttgt acgtatagtt    1140
tttagacaga aaaggaaagt aaattataga gataatgaag tttgctcttt taaattcgtc    1200
gtgatgttat ccatcatatc taaatgctta ttcctgtttt tgtcttttt ctcttttacc    1260 ggagtttatt ttatataatt aattaaagtt agtagatcta tattctttt catagataat    1320 ccatcttctt tggaggcaca tcgatcatta atcatagagt tttgagaagc attatcacta    1380
aagcttcaat taattatatc caataaacgg tattggtgta tgatgttatg atagcaaata    1440
gataatctaa tctatacgag ccacaaaagg ggcatgaact ctatctcgaa gaaattggag    1500
atgaagggat tgagattggc accttgtgct attattgccc actaatcatt             1550
```

<210> SEQ ID NO 3
<211> LENGTH: 12381
<212> TYPE: DNA
<213> ORGANISM: Artificial Sequence
<220> FEATURE:
<223> OTHER INFORMATION: Plasmid sequence of pDAB9582

<400> SEQUENCE: 3

```
agtcagcatc atcacaccaa aagttaggcc cgaatagttt gaaattagaa agctcgcaat    60
tgaggtctac aggccaaatt cgctcttagc cgtacaatat tactcaccgg atcctaaccg    120
gtgtgatcat gggccgcgat taaaaatctc aattatattt ggtctaattt agtttggtat    180
tgagtaaaac aaattcggcg ccatgcccgg gcaagcggcc gcacaagttt gtacaaaaaa    240
gcaggctccg cggtgactga ctgaaaagct tgtcgacctg caggtcaacg gatcaggata    300
ttcttgttta agatgttgaa ctctatggag gtttgtatga actgatgatc taggaccgga    360
taagttccct tcttcatagc gaacttattc aaagaatgtt ttgtgtatca ttcttgttac    420
attgttatta atgaaaaaat attattggtc attggactga acacgagtgt taaatatgga    480
ccaggcccca aataagatcc attgatatat gaattaaata caagaataa atcgagtcac     540 caaaccactt gccttttta acgagacttg ttccaact tgatacaaaa gtcattatcc       600
tatgcaaatc aataatcata caaaaatatc caataacact aaaaaattaa aagaaatgga    660
taatttcaca atatgttata cgataaagaa gttactttc caagaaattc actgatttta    720
```

```
taagcccact tgcattagat aaatggcaaa aaaaaacaaa aaggaaaaga aataaagcac      780
gaagaattct agaaaatacg aaatacgctt caatgcagtg ggacccacgg ttcaattatt      840
gccaattttc agctccaccg tatatttaaa aaataaaacg ataatgctaa aaaaatataa      900
atcgtaacga tcgttaaatc tcaacggctg gatcttatga cgaccgttag aaattgtggt      960
tgtcgacgag tcagtaataa acggcgtcaa agtggttgca gccggcacac acgagtcgtg     1020
tttatcaact caaagcacaa atactttttcc tcaacctaaa aataaggcaa ttagccaaaa    1080
acaactttgc gtgtaaacaa cgctcaatac acgtgtcatt ttattattag ctattgcttc     1140
accgccttag ctttctcgtg acctagtcgt cctcgtcttt tcttcttctt cttctataaa     1200
acaatcccca aagcttcttc ttcacaattc agatttcaat ttctcaaaat cttaaaaact    1260
ttctctcaat tctctctacc gtgatcaagg taaatttctg tgttccttat tctctcaaaa     1320
tcttcgattt tgttttcgtt cgatcccaat ttcgtatatg ttctttggtt tagattctgt     1380
taatcttaga tcgaagacga ttttctgggt ttgatcgtta gatatcatct taattctcga     1440
ttagggtttc ataaatatca tccgatttgt tcaaataatt tgagttttgt cgaataatta    1500
ctcttcgatt tgtgatttct atctagatct ggtgttagtt tctagtttgt gcgatcgaat    1560
ttgtcgatta atctgagttt ttctgattaa cagagatctc catggagaac aatatccaga    1620
accagtgtgt cccatacaat tgcctcaaca atcctgaagt tgagatcctc aacgaagaga    1680
ggagcactgg acgccttccc cttgacatct ccctctccct cacaaggttc cttttgtctg    1740
agtttgttcc tggtgtgggt gtggcctttg gcctctttga cctcatctgg ggcttcatca    1800
ccccatctga ttggagcctc ttccttctcc agattgaaca attgattgag cagaggattg    1860
agacccttga aggaacaga gccatcacca cacttcgtgg ccttgctgac agctatgaaa    1920
tctacattga agcactccgt gagtgggaag ccaatcccaa caatgctcaa ctccgtgaag    1980
atgtgaggat tcgctttgcc aacacagatg acgctttgat cacagccatc aacaatttca    2040
ccctcaccag ctttgagatc cctttgctct cagtctatgt tcaagctgca aacctccact    2100
tgagcttgct tagggatgct gtgtccttcg gacaaggttg gggacttgac atagccactg    2160
tcaacaatca ctacaacaga ctcatcaact tgattcatcg ctacaccaaa cattgcttgg    2220
acacctacaa tcaaggattg gagaacctca gaggcaccaa cactcgccaa tgggcaaggt    2280
tcaaccagtt tagaagggat ctcacactca ctgtgcttga catagttgct ctcttcccca    2340
actatgatgt tcgcacctac ccaattcaaa ccagctccca acttacaagg gaaatctaca    2400
cctcctcagt cattgaggac agcccagttt ctgccaacat acccaatggt ttcaaccgtg    2460
ctgagtttgg tgtcagacca ccccatctca tggacttcat gaactccttg tttgtgactg    2520
ccgagactgt taggtcccaa actgtgtggg gaggccacct tgttagctcc cgcaacaccg    2580
ctggcaaccg catcaacttc ccatcctatg gggttttcaa tcctggtgga gccatctgga    2640
ttgcagatga ggacccaagg cctttctaca gaaccttgtc agatcctgtc tttgtcagag    2700
gaggctttgg caatccacac tatgttcttg gtttgagggg agtggctttt cagcagactg    2760
gcaccaatca caccogcaca ttcagaaaca gcggcaccat tgcagccttt gatgagatcc    2820
cacctcaaga caacagcgga gcaccctgga cgactactc ccatgtgctc aatcatgtca    2880
cctttgtgcg ctggcctggt gagatcagcg gttcagattc ttggagagca ccaatgttct    2940
catggaccca tcgctctgcc acacccacaa acaccattga tccagagaga atcacccaga    3000
ttcccttggt gaaggcacac acacttcagt ctggaaccac agttgtcaga gggcctgggt    3060
tcactggtgg agacattctc agacgcacct ctggagggcc atttgcttac accattgtca    3120
```

```
acatcaatgg gcaacttccc cagcgttacc gtgccagaat ccgctatgct tccaccacta      3180
acttgagaat ctatgtcaca gttgctggtg aaaggatctt tgctggtcag ttcaacaaga      3240
caatggacac tggtgatcca ttgacattcc agtcattctc ctatgccacc atcaacactg      3300
cattcacctt tccaatgagc cagtccagct tcacagtggg tgcagatacc ttcagctccg      3360
gcaatgaggt gtacattgac cgctttgagt tgattccagt gactgccaca cttgaggctg      3420
agtctgactt ggagcgtgct cagaaggccg tgaatgctct cttcacctct tcaaatcaga      3480
ttgggctcaa gacagatgtg actgactacc atatagaccg tgtttccaat cttgttgagt      3540
gcctctctga tgagttctgc ttggatgaga agaaagagtt gtcagagaag gtcaagcacg      3600
ccaagaggct ctctgatgag aggaacttgc ttcaagatcc caacttcaga gggatcaacc      3660
gtcaattgga tcgtggatgg aggggatcaa ctgacataac cattcaagga ggtgacgatg      3720
tgttcaagga gaactatgtc acactcttgg ggacctttga tgagtgctac ccaacatacc      3780
tttaccagaa gatagacgaa agcaagctca aggcctacac aagataccag ttgagaggtt      3840
acattgagga ctctcaagac cttgaaatct acctcatcag atacaacgcc aaacatgaga      3900
cagtcaatgt gcctgggact ggttcactct ggccactttc agccccaagc cccattggca      3960
agtgtgccca tcactcacat cacttctcct tggacataga tgttggctgc actgacttga      4020
atgaggacct tggtgtgtgg gtgatcttca agatcaagac ccaagatggc catgcaaggt      4080
tgggcaatct tgagttctt gaagagaaac cacttgttgg agaagcccct gccagagtga      4140
agagggctga gaagaaatgg agggacaaga gagagaagtt ggagtgggaa caaacattg      4200 tgtacaaaga agccaaagaa tcagttgatg ctttgtttgt gaactcccaa tatgataggc      4260
tccaagctga caccaacata gcaatgattc atgctgcaga caaagggtt cacagcattc      4320 gtgaagcata ccttcctgaa ctctcagtga ttcctggggt caatgctgca atctttgaag      4380
agcttgaagg acgcatcttc actgccttct ccttgtatga tgcaaggaat gtcatcaaga      4440
atggtgactt caacaatggc cttcctgct ggaatgtgaa agggcacgtg gatgttgaag      4500
agcagaacaa tcaccgctct gtccttgttg tccctgagtg ggaagctgaa gtttcacaag      4560
aagttcgtgt ctgccctggt cgtggctaca ttcttcgtgt gactgcttac aaagaaggct      4620
atggagaagg ttgtgtcacc atccacgaga tagagaacaa tactgatgaa ttgaagttca      4680
gcaactgtgt tgaggaagag gtctacccaa acaatactgt cacttgcaat gactacactg      4740
caactcaaga agagtatgag ggcacttaca cttctcgcaa ccgtggctat gatggagcct      4800
atgagagcaa ctcatctgtg cctgctgact atgcttcagc ctatgaagag aaggcataca      4860
ctgatggaag gcgtgacaat ccttgtgaaa gcaacagagg ctatggggac tacacacccc      4920
tcccagctgg ctatgtgacc aaagagttgg agtactttcc tgaaactgac aaggtttgga      4980
ttgagatagg agaaactgaa ggcacattca tagttgactc tgtggagctt ttgctcatgg      5040
aagagtgagt agttagctta atcacctaga gctcggtcac cagcataatt tttattaatg      5100
tactaaatta ctgttttgtt aaatgcaatt ttgctttctc gggatttaa tatcaaaatc      5160 tatttagaaa tacacaatat tttgttgcag gcttgctgga gaatcgatct gctatcataa      5220
aaattacaaa aaaattttat ttgcctcaat tattttagga ttggtattaa ggacgcttaa      5280
attatttgtc gggtcactac gcatcattgt gattgagaag atcagcgata cgaaatattc      5340
gtagtactat cgataattta tttgaaaatt cataagaaaa gcaaacgtta catgaattga      5400
tgaaacaata caaagacaga taaagccacg cacatttagg atattggccg agattactga      5460
atattgagta agatcacgga atttctgaca ggagcatgtc ttcaattcag cccaaatggc      5520
```

```
agttgaaata ctcaaaccgc cccatatgca ggagcggatc attcattgtt tgtttggttg   5580
cctttgccaa catgggagtc caaggttgcg gccgcgcgcc gaaaacaact ttgtatacaa   5640
aagttgccgc ggtgactgac tgaactaaac ccagaaggta attatccaag atgtagcatc   5700
aagaatccaa tgtttacggg aaaaactatg gaagtattat gtaagctcag caagaagcag   5760
atcaatatgc ggcacatatg caacctatgt tcaaaaatga agaatgtaca gatacaagat   5820
cctatactgc cagaatacga agaagaatac gtagaaattg aaaagaaga accaggcgaa    5880 gaaaagaatc ttgaagacgt aagcactgac gacaacaatg aaaagaagaa gataaggtcg   5940
gtgattgtga aagagacata gaggacacat gtaaggtgga aaatgtaagg gcggaaagta   6000
accttatcac aaaggaatct tatcccccac tacttatcct tttatatttt tccgtgtcat   6060
ttttgccctt gagttttcct atataaggaa ccaagttcgg catttgtgaa aacaagaaaa   6120
aatttggtgt aagctatttt ctttgaagta ctgaggatac aacttcagag aaatttgtaa   6180
gtttgtagat ccaacaatgg acaacaatcc aacatcaac gagtgcattc cttacaactg    6240
cctgagcaac cctgaggttg aggtgctggg tggagaacgg attgagactg gttacacacc   6300
tatcgacatc tcgttgtcac ttacccaatt ccttttgtca gagttcgtgc ccggtgctgg   6360
attcgtgctt ggacttgtcg atatcatttg gggaatcttt ggtccctctc aatgggacgc   6420
ctttcttgta cagatagagc agttaattaa ccaaagaata gaagaattcg ctaggaacca   6480
agccatctca aggttagaag gcctcagcaa cctttaccag atttacgcag aatcttttcg   6540
agagtgggaa gcagacccga ccaatcctgc cttaagagag gagatgcgca ttcaattcaa   6600
tgacatgaac agcgcgctga cgaccgcaat tccgctcttc gccgttcaga attaccaagt   6660
tcctctttta tccgtgtacg tgcaggctgc caacctgcac ttgtcggtgc tccgcgatgt   6720
ctccgtgttc ggacaacggt ggggctttga tgccgcaact atcaatagtc gttataatga   6780
tctgactagg cttattggca actataccga ttatgctgtt cgctggtaca cacgggtct    6840 cgaacgtgtc tggggaccgg attctagaga ttgggtcagg tacaaccagt tcaggcgaga   6900
gttgacacta actgtcctag acattgtcgc tctcttccc aactacgact ctaggcgcta    6960
cccaatccgt actgtgtcac aattgacccg ggaaatctac acaaacccag tcctcgagaa   7020
cttcgacggt agcttttcgag gctcggctca gggcatagag agaagcatca ggtctccaca   7080
cctgatggac atattgaaca gtatcacgat ctacaccgat gcgcaccgcg gttattacta   7140
ctggtcaggg catcagatca tggcatcacc cgttgggttc tctggaccag aattcacttt   7200
cccactttac gggactatgg gcaatgcagc tccacaacaa cgtattgttg ctcaactcgg   7260
tcagggcgtg tatagaacct tgtccagcac tctatatagg agaccttca acatcggcat    7320 caacaatcaa caattgtctg tgcttgacgg gacagaattt gcctatggaa cctcctcaaa   7380
tctgccatcc gctgtctaca gaaagagcgg aacagttgat agcttggatg agatccctcc   7440
acagaacaac aacgttccac ctaggcaagg gtttagccat cgccttagcc atgtgtccat   7500
gttccgttca ggctttagta atagcagcgt tagtatcatc agagctccga tgttctcttg   7560
gatacatcgt agtgctgagt ttaacaacat aattgcatcc gatagcatta ctcagatccc   7620
agctgtcaag gggaactttc tctttaatgg ttctgtcatt tcaggaccag gattcactgg   7680
aggcgacttg gttaggctga attcttccgg caacaacatc cagaatagag ggtatattga   7740 agtgccatt cacttcccat cgacatctac cagatatcgt gttcgtgtaa ggtatgcctc     7800
tgttacccct attcacctca cgtcaattg gggtaattcc tccatctttt ccaatacagt    7860
accagcgaca gctacatcct tggataatct ccaatctagc gatttcggtt acttcgaaag   7920
```

| | |
|---|---|
| tgccaatgcc ttcacctctt ccctaggtaa catagtaggt gttagaaatt tctccggaac | 7980 |
| cgccggagtg ataatcgacc gcttcgaatt cattcccgtt actgcaacgc tcgaggcaga | 8040 |
| gtctgacttg gaaagagcac agaaggcggt gaatgctctg ttcacttcgt ccaatcagat | 8100 |
| tgggctcaag acagatgtga ctgactatca catcgatcgc gtttccaacc ttgttgagtg | 8160 |
| cctctctgat gagttctgtt tggatgagaa gaaggagttg tccgagaagg tcaaacatgc | 8220 |
| taagcgactt agtgatgagc ggaacttgct tcaagatccc aactttcgcg ggatcaacag | 8280 |
| gcaactagat cgtggatgga ggggaagtac ggacatcacc attcaaggag gtgatgatgt | 8340 |
| gttcaaggag aactatgtta cgctcttggg tacctttgat gagtgctatc caacatacct | 8400 |
| gtaccagaag atagatgaat cgaaactcaa agcctacaca agataccagt tgagaggtta | 8460 |
| catcgaggac agtcaagacc ttgagatcta cctcatcaga tacaacgcca aacatgagac | 8520 |
| agtcaatgtg cctgggacgg gttcactctg gccactttca gccccaagtc ccatcggcaa | 8580 |
| gtgtgcccat cactcacacc acttctcctt ggacatagac gttggctgta ccgacctgaa | 8640 |
| cgaagacctc ggtgtgtggg tgatcttcaa gatcaagact caagatggcc atgccaggct | 8700 |
| aggcaatctg gagtttctag aagagaaacc acttgttgga gaagccctcg ctagagtgaa | 8760 |
| gagggctgag aagaagtgga gggacaagag agagaagttg gaatgggaaa caaacattgt | 8820 |
| gtacaaagaa gccaaagaaa gcgttgacgc tctgtttgtg aactctcagt atgataggct | 8880 |
| ccaagctgat accaacatag ctatgattca tgctgcagac aaacgcgttc atagcattcg | 8940 |
| ggaagcttac cttcctgaac ttagcgtgat tccgggtgtc aatgctgcta tctttgaaga | 9000 |
| gttagaaggg cgcatcttca ctgcattctc cttgtatgat gcgaggaatg tcatcaagaa | 9060 |
| tggtgacttc aacaatggcc tatcctgctg gaatgtgaaa gggcacgtag atgtagaaga | 9120 |
| acagaacaat caccgctctg tccttgttgt tcctgagtgg gaagcagaag tttcacaaga | 9180 |
| agttcgtgtc tgtcctggtc gtggctacat tcttcgtgtt accgcgtaca aagaaggata | 9240 |
| cggagaaggt tgcgtcacca tacacgagat tgagaacaac accgacgagc tgaagttcag | 9300 |
| caactgcgtc gaggaggaag tctacccaaa caacaccgta acttgcaatg actacactgc | 9360 |
| gactcaagag gagtatgagg gtacttacac ttctcgcaat cgaggatacg atggagccta | 9420 |
| tgagagcaac tcttctgtac ccgctgacta tgcatcagcc tatgaggaga aggcttacac | 9480 |
| cgatggacgt agggacaatc cttgcgaatc taacagaggc tatgggact acacaccgtt | 9540 |
| accagccggc tatgtcacca aagagttaga gtactttcca gaaaccgaca aggtttggat | 9600 |
| tgagattgga gaaacggaag gaacattcat tgttgatagc gtggagttac ttctgatgga | 9660 |
| ggaatgagta gttagcttaa tcacctagag ctcggttacc tatcaaaatc tatttagaaa | 9720 |
| tacacaatat tttgttgcag gcttgctgga gaatcgatct gctatcataa aaattacaaa | 9780 |
| aaaattttat ttgcctcaat tattttagga ttggtattaa ggacgcttaa attatttgtc | 9840 |
| gggtcactac gcatcattgt gattgagaag atcagcgata cgaaatattc gtagtactat | 9900 |
| cgataattta tttgaaaatt cataagaaaa gcaaacgtta catgaattga tgaaacaata | 9960 |
| caaagacaga taaagccacg cacatttagg atattggccg agattactga atattgagta | 10020 |
| agatcacgga atttctgaca ggagcatgtc ttcaattcag cccaaatggc agttgaaata | 10080 |
| ctcaaaccgc cccatatgca ggagcggatc attcattgtt tgtttggttg cctttgccaa | 10140 |
| catgggagtc caaggttgcg gccgcgcgcc gacccagctt tcttgtacaa agtggttgcg | 10200 |
| gccgcttaat taaattttaaa tgcccgggcg tttaaacgcg gccgcttaat taaggccggc | 10260 |
| ctgcagcaaa cccagaaggt aattatccaa gatgtagcat caagaatcca atgtttacgg | 10320 |

```
gaaaaactat ggaagtatta tgtaagctca gcaagaagca gatcaatatg cggcacatat    10380
gcaacctatg ttcaaaaatg aagaatgtac agatacaaga tcctatactg ccagaatacg    10440
aagaagaata cgtagaaatt gaaaagaag  aaccaggcga agaaaagaat cttgaagacg    10500
taagcactga cgacaacaat gaaaagaaga agataaggtc ggtgattgtg aaagagacat    10560
agaggacaca tgtaaggtgg aaaatgtaag ggcggaaagt aaccttatca caaaggaatc    10620
ttatccccca ctacttatcc ttttatattt ttccgtgtca tttttgccct tgagttttcc    10680
tatataagga accaagttcg gcatttgtga aaacaagaaa aaatttggtg taagctatttt   10740 tctttgaagt actgaggata caacttcaga gaaatttgta agtttgtaga tctccatgtc    10800
tccggagagg agaccagttg agattaggcc agctacagca gctgatatgg ccgcggtttg    10860
tgatatcgtt aaccattaca ttgagacgtc tacagtgaac tttaggacag agccacaaac    10920
accacaagag tggattgatg atctagagag gttgcaagat agatacccctt ggttggttgc   10980 tgaggttgag ggtgttgtgg ctggtattgc ttacgctggg ccctggaagg ctaggaacgc    11040
ttacgattgg acagttgaga gtactgttta cgtgtcacat aggcatcaaa ggttgggcct    11100
aggatccaca ttgtacacac atttgcttaa gtctatggag gcgcaaggtt ttaagtctgt    11160
ggttgctgtt ataggccttc caaacgatcc atctgttagg ttgcatgagg ctttgggata    11220
cacagcccgg ggtacattgc gcgcagctgg atacaagcat ggtggatggc atgatgttgg    11280 ttttttggcaa agggattttg agttgccagc tcctccaagg ccagttaggc cagttaccca   11340
gatctgaggt accctgagct tgagcttatg agcttatgag cttagagctc ggatccacta    11400
gtaacggccg ccagtgtgct ggaattcgcc cttgactaga taggcgccca gatcggcggc    11460
aatagcttct tagcgccatc ccgggttgat cctatctgtg ttgaaatagt tgcggtgggc    11520
aaggctctct ttcagaaaga caggcggcca aaggaaccca aggtgaggtg ggctatggct    11580
ctcagttcct tgtggaagcg cttggtctaa ggtgcagagg tgttagcggg atgaagcaaa    11640
agtgtccgat tgtaacaaga tatgttgatc ctacgtaagg atattaaagt atgtattcat    11700
cactaatata atcagtgtat tccaatatgt actacgattt ccaatgtctt tattgtcgcc    11760
gtatgtaatc ggcgtcacaa aataatcccc ggtgactttc ttttaatcca ggatgaaata    11820
atatgttatt ataatttttg cgatttggtc cgttatagga attgaagtgt gcttgcggtc    11880
gccaccactc ccatttcata attttacatg tatttgaaaa ataaaaattt atggtattca    11940
atttaaacac gtatacttgt aaagaatgat atcttgaaag aaatatagtt taaatattta    12000
ttgataaaat aacaagtcag gtattatagt ccaagcaaaa acataaattt attgatgcaa    12060
gtttaaattc agaaatattt caataactga ttatatcagc tggtacattg ccgtagatga    12120
aagactgagt gcgatattat ggtgtaatac atagcggccg ggtttctagt caccggttag    12180
gatccgttta aactcgaggc tagcgcatgc acatagacac acacatcatc tcattgatgc    12240
ttggtaataa ttgtcattag attgttttta tgcatagatg cactcgaaat cagccaattt    12300
tagacaagta tcaaacggat gtgacttcag tacattaaaa acgtccgcaa tgtgttatta    12360
agttgtctaa gcgtcaattt g                                              12381
```

<210> SEQ ID NO 4
<211> LENGTH: 30
<212> TYPE: DNA
<213> ORGANISM: Artificial Sequence
<220> FEATURE:
<223> OTHER INFORMATION: 81419_FW3 Primer

<400> SEQUENCE: 4

```
tttctcctat ccgtcaaata aatctgctcc                                    30

<210> SEQ ID NO 5
<211> LENGTH: 27
<212> TYPE: DNA
<213> ORGANISM: Artificial Sequence
<220> FEATURE:
<223> OTHER INFORMATION: 81419_RV1 primer

<400> SEQUENCE: 5
gggtgatttg gtgccaaaag ttatgtt                                       27

<210> SEQ ID NO 6
<211> LENGTH: 24
<212> TYPE: DNA
<213> ORGANISM: Artificial Sequence
<220> FEATURE:
<223> OTHER INFORMATION: 81419_RV2 primer

<400> SEQUENCE: 6
tggagggtca tatcgcaaaa gact                                          24

<210> SEQ ID NO 7
<211> LENGTH: 24
<212> TYPE: DNA
<213> ORGANISM: Artificial Sequence
<220> FEATURE:
<223> OTHER INFORMATION: 81419_RV3 primer

<400> SEQUENCE: 7
gttctgcgtc gtggagggtc atat                                          24

<210> SEQ ID NO 8
<211> LENGTH: 29
<212> TYPE: DNA
<213> ORGANISM: Artificial Sequence
<220> FEATURE:
<223> OTHER INFORMATION: 5'IREnd-01 primer

<400> SEQUENCE: 8
cgagctttct aatttcaaac tattcgggc                                     29

<210> SEQ ID NO 9
<211> LENGTH: 30
<212> TYPE: DNA
<213> ORGANISM: Artificial Sequence
<220> FEATURE:
<223> OTHER INFORMATION: 5'IREnd-02 primer

<400> SEQUENCE: 9
tcctagatca tcagttcata caaacctcca                                    30

<210> SEQ ID NO 10
<211> LENGTH: 29
<212> TYPE: DNA
<213> ORGANISM: Artificial Sequence
<220> FEATURE:
<223> OTHER INFORMATION: AtUbi10RV1 primer

<400> SEQUENCE: 10
cggtcctaga tcatcagttc atacaaacc                                     29

<210> SEQ ID NO 11
<211> LENGTH: 28
<212> TYPE: DNA
<213> ORGANISM: Artificial Sequence
```

```
<220> FEATURE:
<223> OTHER INFORMATION: AtUbi10RV2 primer

<400> SEQUENCE: 11
cactcgtgtt cagtccaatg accaataa                                              28

<210> SEQ ID NO 12
<211> LENGTH: 20
<212> TYPE: DNA
<213> ORGANISM: Artificial Sequence
<220> FEATURE:
<223> OTHER INFORMATION: 3'PATEnd05 primer

<400> SEQUENCE: 12
gctcctccaa ggccagttag                                                       20

<210> SEQ ID NO 13
<211> LENGTH: 20
<212> TYPE: DNA
<213> ORGANISM: Artificial Sequence
<220> FEATURE:
<223> OTHER INFORMATION: 3'PATEnd06 primer

<400> SEQUENCE: 13
ccagttaggc cagttaccca                                                       20

<210> SEQ ID NO 14
<211> LENGTH: 15294
<212> TYPE: DNA
<213> ORGANISM: Artificial Sequence
<220> FEATURE:
<223> OTHER INFORMATION: Sequence of soybean event 9582.814.19.1

<400> SEQUENCE: 14
ttaacaatga ccaagattta tgctatatag aagacttgga gggcttaagg ctatgatata           60
ttatggatga tatggttctg atttgtgtag tttcgaagga tcaaatcaac catttgttgg          120
tacaatggga agaaaaaatg ttttcatcat tccactctat tgaaaaagat ccaacaattg          180
taacaccccg acgaatcaca ccggaaagag aagaatccaa agattgtgta ggtatgagac          240
tgtatagttg atgaaaactt aaaaaaatta attggtacta cttataccaa caagatgcat          300 atattttcg atagcctatc acataagaac ttcatagtta agggtgctta acttggagta           360
gttatgaaat gagtgacctt ttaaaataat tattgtctta ggttattgta tgaaaataaa          420
aaataataat aaatatacat aaaaaatat aatttataa aattaacctt atattatcat            480
taatttattt ttagattttg ttattcatta ttaatatatg aggtataaat gaaaaatata          540
attaatgtca cattaaaaaa ttaaaatgat aattattttg aaacaaatta tttattttta          600
tacgacaatt ataatagaaa tttgagagta aaaaaaaatt gaaaattcat aaaatatatg          660
aatatattca tttctcctat ccgtcaaata aatctgctcc ataatttatc taagcattgg          720
tcttgtagtt cagagtaata aaattttagc aattattagt tagtacagat acatttaaag          780
aaataatata ttttagcaac tagaagttta taaaagtttt taaattataa agacttatat          840
ataaatttag taaaactaga tggatgtccc aagtaatttt tatataacta ttctcgtaca          900
acattaatga aaatcttgtt tctattattt atatgtatat tattatttta ttttggaaca          960
atatgggatt aaaaactctt ataaattaaa tcttagaata agttttccta acatgttttt         1020
tttatggatg ttttcctaac atgtttggtt atcttagttg tgctttaatt ttgtcggatt         1080
atttttggac tttattaggt aattttgata aaacttttag ttgatgttag tagtttactc         1140
ttacataatg atttgatatt gaatgtgtat aattggaagg caataaatga agatcaagcg         1200
```

```
tacaagagtt cgccaatcaa gaggatttga agagagtaaa atattatgcg aagtcccatg    1260
tgaagaaaat ccaaccattg gaataaaaaa taaagttttt tctttggaat tgctaatgct    1320
acagcactta ttggtacttg tcctaaaaat gaaactctag ctatatttag cacttgatat    1380
tcatgaatca aacttctcta tgaaataacc gcggtgcgca tcggtgcctg ttgatcccgc    1440
gcaagtgggg atcttgaagc aagttccgct catcactaag tcgcttagca tgtttgacct    1500
tctcggacaa ctccttcttc tctttaattg atcaacagtc agcatcatca caccaaaagt    1560
taggcccgaa tagtttgaaa ttagaaagct cgcaattgag gtctacaggc caaattcgct    1620
cttagccgta caatattact caccggatcc taaccggtgt gatcatgggc cgcgattaaa    1680
aatctcaatt atatttggtc taatttagtt tggtattgag taaaacaaat tcggcgccat    1740
gcccgggcaa gcggccgcac aagtttgtac aaaaaagcag gctccgcggt gactgactga    1800
aaagcttgtc gacctgcagg tcaacggatc aggatattct tgtttaagat gttgaactct    1860
atggaggttt gtatgaactg atgatctagg accggataag ttcccttctt catagcgaac    1920
ttattcaaag aatgttttgt gtatcattct tgttacattg ttattaatga aaaaatatta    1980
ttggtcattg gactgaacac gagtgttaaa tatggaccag gccccaaata agatccattg    2040
atatatgaat taaataacaa gaataaatcg agtcaccaaa ccacttgcct tttttaacga    2100
gacttgttca ccaacttgat acaaaagtca ttatcctatg caaatcaata atcatacaaa    2160
aatatccaat aacactaaaa aattaaaaga atggataat ttcacaatat gttatacgat    2220
aaagaagtta cttttccaag aaattcactg attttataag cccacttgca ttagataaat    2280
ggcaaaaaaa aacaaaaagg aaaagaaata aagcacgaag aattctagaa aatacgaaat    2340
acgcttcaat gcagtgggac ccacggttca attattgcca attttcagct ccaccgtata    2400
tttaaaaaat aaaacgataa tgctaaaaaa atataaatcg taacgatcgt taaatctcaa    2460
cggctggatc ttatgacgac cgttagaaat tgtggttgtc gacgagtcag taataaacgg    2520
cgtcaaagtg gttgcagccg gcacacacga gtcgtgttta tcaactcaaa gcacaaatac    2580
ttttcctcaa cctaaaaata aggcaattag ccaaaaacaa ctttgcgtgt aaacaacgct    2640
caatacacgt gtcattttat tattagctat tgcttcaccg ccttagcttt ctcgtgacct    2700
agtcgtcctc gtcttttctt cttcttcttc tataaaacaa tacccaaagc ttcttcttca    2760
caattcagat ttcaatttct caaaatctta aaaactttct ctcaattctc tctaccgtga    2820
tcaaggtaaa tttctgtgtt ccttattctc tcaaaatctt cgattttgtt ttcgttcgat    2880
cccaatttcg tatatgttct ttggtttaga ttctgttaat cttagatcga agacgatttt    2940
ctgggtttga tcgttagata tcatcttaat tctcgattag ggtttcataa atatcatccg    3000
atttgttcaa ataatttgag ttttgtcgaa taattactct tcgatttgtg atttctatct    3060
agatctggtg ttagttttcta gtttgtgcga tcgaatttgt cgattaatct gagtttttct    3120
gattaacaga gatctccatg gagaacaata tccagaacca gtgtgtccca tacaattgcc    3180
tcaacaatcc tgaagttgag atcctcaacg aagagaggag cactggacgc cttcccttg    3240 acatctccct ctccctcaca aggttccttt tgtctgagtt tgttcctggt gtgggtgtgg    3300
cctttggcct ctttgacctc atctgggct tcatcacccc atctgattgg agcctcttcc    3360
ttctccagat tgaacaattg attgagcaga ggattgagac ccttgaaagg aacagagcca    3420
tcaccacact tcgtggcctt gctgacagct atgaaatcta cattgaagca ctccgtgagt    3480
gggaagccaa tcccaacaat gctcaactcc gtgaagatgt gaggattcgc tttgccaaca    3540
cagatgacgc tttgatcaca gccatcaaca atttcaccct caccagcttt gagatccctt    3600
```

```
tgctctcagt ctatgttcaa gctgcaaacc tccacttgag cttgcttagg gatgctgtgt   3660
ccttcggaca aggttgggga cttgacatag ccactgtcaa caatcactac aacagactca   3720
tcaacttgat tcatcgctac accaaacatt gcttggacac ctacaatcaa ggattggaga   3780
acctcagagg caccaacact cgccaatggg caaggttcaa ccagtttaga agggatctca   3840
cactcactgt gcttgacata gttgctctct tccccaacta tgatgttcgc acctacccaa   3900
ttcaaaccag ctcccaactt acaagggaaa tctacacctc ctcagtcatt gaggacagcc   3960
cagtttctgc caacataccc aatggtttca accgtgctga gtttggtgtc agaccacccc   4020
atctcatgga cttcatgaac tccttgtttg tgactgccga gactgttagg tcccaaactg   4080
tgtggggagg ccaccttgtt agctcccgca acaccgctgg caaccgcatc aacttcccat   4140 cctatgggt tttcaatcct ggtggagcca tctggattgc agatgaggac ccaaggcctt   4200
tctacagaac cttgtcagat cctgtctttg tcagaggagg cttttggcaat ccacactatg   4260 ttcttggttt gagggagtg gcttttcagc agactggcac caatcacacc cgcacattca   4320
gaaacagcgg caccattgac agccttgatg agatcccacc tcaagacaac agcggagcac   4380 cctgaacga ctactcccat gtgctcaatc atgtcacctt tgtgcgctgg cctggtgaga   4440
tcagcggttc agattcttgg agagcaccaa tgttctcatg gacccatcgc tctgccacac   4500
ccacaaacac cattgatcca gagagaatca cccagattcc cttggtgaag gcacacacac   4560
ttcagtctgg aaccacagtt gtcagagggc ctgggttcac tggtggagac attctcagac   4620
gcacctctgg agggccattt gcttacacca ttgtcaacat caatgggcaa cttccccagc   4680
gttaccgtgc cagaatccgc tatgcttcca ccactaactt gagaatctat gtcacagttg   4740
ctggtgaaag gatcttttgct ggtcagttca caagacaat ggacactggt gatccattga   4800
cattccagtc attctcctat gccaccatca acactgcatt caccttttcca atgagccagt   4860 ccagcttcac agtgggtgca gatacccttca gctccggcaa tgaggtgtac attgaccgct   4920
ttgagttgat tccagtgact gccacacttg aggctgagtc tgacttggag cgtgctcaga   4980
aggccgtgaa tgctctcttc acctcttcaa atcagattgg gctcaagaca gatgtgactg   5040
actaccatat agaccgtgtt tccaatcttg ttgagtgcct ctctgatgag ttctgcttgg   5100
atgagaagaa agagttgtca gagaaggtca agcacgccaa gaggctctct gatgagagga   5160
acttgcttca agatcccaac ttcagaggga tcaaccgtca attggatcgt ggatggaggg   5220
gatcaactga cataaccatt caaggaggtg acgatgtgtt caaggagaac tatgtcacac   5280
tcttggggac cttttgatgag tgctacccaa catacctta ccagaagata gacgaaagca   5340
agctcaaggc ctacacaaga taccagttga gaggttacat tgaggactct caagaccttg   5400
aaatctacct catcagatac aacgccaaac atgagacagt caatgtgcct gggactggtt   5460
cactctggcc acttttcagcc ccaagcccca ttggcaagtg tgcccatcac tcacatcact   5520
tctccttgga catagatgtt ggctgcactg acttgaatga ggaccttggt gtgtgggtga   5580
tcttcaagat caagacccaa gatggccatg caaggttggg caatcttgag tttcttgaag   5640
agaaaccact tgttggagaa gcccttgcca gagtgaagag ggctgagaag aaatggaggg   5700
acaagagaga gaagttggag tgggaaacaa acattgtgta caaagaagcc aaagaatcag   5760
ttgatgcttt gtttgtgaac tcccaatatg ataggctcca agctgacacc aacatagcaa   5820
tgattcatgc tgcagacaaa agggttcaca gcattcgtga agcataccct cctgaactct   5880
cagtgattcc tggggtcaat gctgcaatct ttgaagagct tgaaggacgc atcttcactg   5940
ccttctcctt gtatgatgca aggaatgtca tcaagaatgg tgacttcaac aatggccttt   6000
```

```
cctgctggaa tgtgaaaggg cacgtggatg ttgaagagca gaacaatcac cgctctgtcc    6060
ttgttgtccc tgagtgggaa gctgaagttt cacaagaagt tcgtgtctgc cctggtcgtg    6120
gctacattct tcgtgtgact gcttacaaag aaggctatgg agaaggttgt gtcaccatcc    6180
acgagataga gaacaatact gatgaattga agttcagcaa ctgtgttgag gaagaggtct    6240
acccaaacaa tactgtcact tgcaatgact acactgcaac tcaagaagag tatgagggca    6300
cttacacttc tcgcaaccgt ggctatgatg gagcctatga gagcaactca tctgtgcctg    6360
ctgactatgc ttcagcctat gaagagaagg catacactga tggaaggcgt gacaatcctt    6420
gtgaaagcaa cagaggctat ggggactaca caccccctccc agctggctat gtgaccaaag    6480
agttggagta ctttcctgaa actgacaagg tttggattga gataggagaa actgaaggca    6540
cattcatagt tgactctgtg gagcttttgc tcatggaaga gtgagtagtt agcttaatca    6600
cctagagctc ggtcaccagc ataatttttta ttaatgtact aaattactgt tttgttaaat    6660 gcaatttttgc tttctcggga ttttaatatc aaaatctatt tagaaataca caatattttg    6720
ttgcaggctt gctggagaat cgatctgcta tcataaaaat tacaaaaaaa ttttatttgc    6780
ctcaattatt ttaggattgg tattaaggac gcttaaatta tttgtcgggt cactacgcat    6840
cattgtgatt gagaagatca gcgatacgaa atattcgtag tactatcgat aatttatttg    6900
aaaattcata agaaaagcaa acgttacatg aattgatgaa acaatacaaa gacagataaa    6960
gccacgcaca tttaggatat tggccgagat tactgaatat tgagtaagat cacggaattt    7020
ctgacaggag catgtcttca attcagccca aatggcagtt gaaatactca aaccgcccca    7080
tatgcaggag cggatcattc attgtttgtt tggttgcctt tgccaacatg ggagtccaag    7140
gttgcggccg cgcgccgaaa caactttgt atacaaagt tgccgcggtg actgactgaa    7200
ctaaacccag aaggtaatta tccaagatgt agcatcaaga atccaatgtt tacgggaaaa    7260 actatgaag tattatgtaa gctcagcaag aagcagatca atatgcggca catatgcaac    7320
ctatgttcaa aaatgaagaa tgtacagata caagatccta tactgccaga atacgaagaa    7380
gaatacgtag aaattgaaaa agaagaacca ggcgaagaaa agaatcttga agacgtaagc    7440
actgacgaca acaatgaaaa gaagaagata aggtcggtga ttgtgaaaga gacatagagg    7500
acacatgtaa ggtggaaaat gtaagggcgg aaagtaacct tatcacaaag gaatcttatc    7560
ccccactact tatcctttta tattttttccg tgtcattttt gcccttgagt tttcctatat    7620
aaggaaccaa gttcggcatt tgtgaaaaca agaaaaaatt tggtgtaagc tatttctttt    7680
gaagtactga ggatacaact tcagagaaat ttgtaagttt gtagatccaa caatggacaa    7740
caatcccaac atcaacgagt gcattcctta caactgcctg agcaaccctg aggttgaggt    7800
gctgggtgga gaacggattg agactggtta cacacctatc gacatctcgt tgtcacttac    7860
ccaattcctt ttgtcagagt tcgtgcccgg tgctggattc gtgcttggac ttgtcgatat    7920
catttgggga atctttggtc cctctcaatg ggacgccttt cttgtacaga tagagcagtt    7980
aattaaccaa agaatagaag aattcgctag gaaccaagcc atctcaaggt tagaaggcct    8040
cagcaacctt taccagattt acgcagaatc ttttcgagag tgggaagcag acccgaccaa    8100
tcctgcctta agagaggaga tgcgcattca attcaatgac atgaacagcg cgctgacgac    8160
cgcaattccg ctcttcgccg ttcagaatta ccaagttcct ctttttatccg tgtacgtgca    8220 ggctgccaac ctgcacttgt cggtgctccg cgatgtctcc gtgttcggac aacggtgggg    8280 cttttgatgcc gcaactatca atagtcgtta taatgatctg actaggctta ttggcaacta    8340
taccgattat gctgttcgct ggtacaacac gggtctcgaa cgtgtctggg gaccggattc    8400
```

```
tagagattgg gtcaggtaca accagttcag gcgagagttg acactaactg tcctagacat    8460
tgtcgctctc tttcccaact acgactctag gcgctaccca atccgtactg tgtcacaatt    8520
gacccgggaa atctacacaa acccagtcct cgagaacttc gacggtagct ttcgaggctc    8580
ggctcagggc atagagagaa gcatcaggtc tccacacctg atggacatat tgaacagtat    8640
cacgatctac accgatgcgc accgcggtta ttactactgg tcagggcatc agatcatggc    8700
atcacccgtt gggttctctg gaccagaatt cactttccca ctttacggga ctatgggcaa    8760
tgcagctcca caacaacgta ttgttgctca actcggtcag ggcgtgtata gaaccttgtc    8820
cagcactcta tataggagac ctttcaacat cggcatcaac aatcaacaat tgtctgtgct    8880
tgacgggaca gaatttgcct atggaacctc ctcaaatctg ccatccgctg tctacagaaa    8940
gagcggaaca gttgatagct tggatgagat ccctccacag aacaacaacg ttccacctag    9000
gcaagggttt agccatcgcc ttagccatgt gtccatgttc cgttcaggct ttagtaatag    9060
cagcgttagt atcatcagag ctccgatgtt ctcttggata catcgtagtg ctgagtttaa    9120
caacataatt gcatccgata gcattactca gatcccagct gtcaagggga actttctctt    9180
taatggttct gtcatttcag gaccaggatt cactggaggc gacttggtta ggctgaattc    9240
ttccggcaac aacatccaga atagagggta tattgaagtg cccattcact tcccatcgac    9300
atctaccaga tatcgtgttc gtgtaaggta tgcctctgtt accccctattc acctcaacgt    9360
caattggggt aattcctcca tcttttccaa tacagtacca gcgacagcta catccttgga    9420
taatctccaa tctagcgatt tcggttactt cgaaagtgcc aatgccttca cctcttccct    9480
aggtaacata gtaggtgtta gaaatttctc cggaaccgcc ggagtgataa tcgaccgctt    9540
cgaattcatt cccgttactg caacgctcga ggcagagtct gacttggaaa gagcacagaa    9600
ggcggtgaat gctctgttca cttcgtccaa tcagattggg ctcaagacag atgtgactga    9660
ctatcacatc gatcgcgttt ccaaccttgt tgagtgcctc tctgatgagt tctgtttgga    9720
tgagaagaag gagttgtccg agaaggtcaa acatgctaag cgacttagtg atgagcggaa    9780
cttgcttcaa gatcccaact ttcgcgggat caacaggcaa ctagatcgtg gatggagggg    9840
aagtacggac atcaccattc aaggaggtga tgatgtgttc aaggagaact atgttacgct    9900
cttgggtacc tttgatgagt gctatccaac atacctgtac cagaagatag atgaatcgaa    9960
actcaaagcc tacacaagat accagttgag aggttacatc gaggacagtc aagaccttga   10020
gatctacctc atcagataca acgccaaaca tgagacagtc aatgtgcctg ggacgggttc   10080
actctggcca ctttcagccc caagtcccat cggcaagtgt gcccatcact cacaccactt   10140
ctccttggac atagacgttg gctgtaccga cctgaacgaa gacctcggtg tgtgggtgat   10200
cttcaagatc aagactcaag atggccatgc caggctaggc aatctggagt ttctagaaga   10260
gaaaccactt gttggagaag ccctcgctag agtgaagagg gctgagaaga agtggaggga   10320
caagagagag aagttggaat gggaaacaaa cattgtgtac aaagaagcca agaaagcgt   10380
tgacgctctg tttgtgaact ctcagtatga taggctccaa gctgatacca acatagctat   10440
gattcatgct gcagacaaac gcgttcatag cattcgggaa gcttaccttc ctgaacttag   10500
cgtgattccg ggtgtcaatg ctgctatctt tgaagagtta aagggcgca tcttcactgc   10560
attctccttg tatgatgcga ggaatgtcat caagaatggt gacttcaaca atggcctatc   10620
ctgctggaat gtgaaagggc acgtagatgt agaagaacag aacaatcacc gctctgtcct   10680
tgttgttcct gagtgggaag cagaagtttc acaagaagtt cgtgtctgtc ctggtcgtgg   10740
ctacattctt cgtgttaccg cgtacaaaga aggatacgga gaaggttgcg tcaccataca   10800
```

```
cgagattgag aacaacaccg acgagctgaa gttcagcaac tgcgtcgagg aggaagtcta   10860
cccaaacaac accgtaactt gcaatgacta cactgcgact caagaggagt atgagggtac   10920
ttacacttct cgcaatcgag gatacgatgg agcctatgag agcaactctt ctgtacccgc   10980
tgactatgca tcagcctatg aggagaaggc ttacaccgat ggacgtaggg acaatccttg   11040
cgaatctaac agaggctatg gggactacac accgttacca gccggctatg tcaccaaaga   11100
gttagagtac tttccagaaa ccgacaaggt ttggattgag attggagaaa cggaaggaac   11160
attcattgtt gatagcgtgg agttacttct gatggaggaa tgagtagtta gcttaatcac   11220
ctagagctcg gttacctatc aaaatctatt tagaaataca caatattttg ttgcaggctt   11280
gctggagaat cgatctgcta tcataaaaat tacaaaaaaa ttttatttgc ctcaattatt   11340
ttaggattgg tattaaggac gcttaaatta tttgtcgggt cactacgcat cattgtgatt   11400
gagaagatca gcgatacgaa atattcgtag tactatcgat aatttatttg aaaattcata   11460
agaaaagcaa acgttacatg aattgatgaa acaatacaaa gacagataaa gccacgcaca   11520
tttaggatat tggccgagat tactgaatat tgagtaagat cacggaattt ctgacaggag   11580
catgtcttca attcagccca aatggcagtt gaaatactca aaccgcccca tatgcaggag   11640
cggatcattc attgtttgtt tggttgcctt tgccaacatg ggagtccaag gttgcggccg   11700
cgcgccgacc cagcttttct gtacaaagtg gttgcggccg cttaattaaa tttaaatgcc   11760
cgggcgttta acgcggccg cttaattaag gccggcctgc agcaaaccca gaaggtaatt   11820
atccaagatg tagcatcaag aatccaatgt ttacgggaaa aactatggaa gtattatgta   11880
agctcagcaa gaagcagatc aatatgcggc acatatgcaa cctatgttca aaaatgaaga   11940
atgtacagat acaagatcct atactgccag aatacgaaga agaatacgta gaaattgaaa   12000
aagaagaacc aggcgaagaa aagaatcttg aagacgtaag cactgacgac aacaatgaaa   12060
agaagaagat aaggtcggtg attgtgaaag agacatagag gacacatgta aggtggaaaa   12120
tgtaagggcg gaaagtaacc ttatcacaaa ggaatcttat cccccactac ttatcctttt   12180
atatttttcc gtgtcatttt tgcccttgag ttttcctata taaggaacca agttcggcat   12240
ttgtgaaaac aagaaaaaat ttggtgtaag ctattttctt tgaagtactg aggatacaac   12300
ttcagagaaa tttgtaagtt tgtagatctc catgtctccg gagaggagac cagttgagat   12360
taggccagct acagcagctg atatggccgc ggtttgtgat atcgttaacc attacattga   12420
gacgtctaca gtgaacttta ggacagagcc acaaacacca caagagtgga ttgatgatct   12480
agagaggttg caagatagat acccttggtt ggttgctgag gttgagggtg ttgtggctgg   12540
tattgcttac gctgggccct ggaaggctag gaacgcttac gattggacag ttgagagtac   12600
tgtttacgtg tcacataggc atcaaaggtt gggcctagga tccacattgt acacacattt   12660
gcttaagtct atggaggcgc aaggttttaa gtctgtggtt gctgttatag gccttccaaa   12720
cgatccatct gttaggttgc atgaggcttt gggatacaca gcccggggta cattgcgcgc   12780
agctggatac aagcatggtg gatgcatgal tgttggtttt tggcaaaggg attttgagtt   12840
gccagctcct ccaaggccag ttaggccagt tacccagatc tgaggtaccc tgagcttgag   12900
cttatgagct tatgagctta gagctcggat ccactagtaa cggccgccag tgtgctggaa   12960
ttcgcccttg actagatagg cgcccagatc ggcggcaata gcttcttagc gccatcccgg   13020
gttgatccta tctgtgttga aatagttgcg gtgggcaagg ctctctttca gaaagacagg   13080
cggccaaagg aacccaaggt gaggtgggct atggctctca gttccttgtg gaagcgcttg   13140
gtctaaggtg cagaggtgtt agcgggatga agcaaaagtg tccgattgta acaagatatg   13200
```

-continued

```
ttgatcctac gtaaggatat taaagtatgt attcatcact aatataatca gtgtattcca  13260
atatgtacta cgatttccaa tgtctttatt gtcgccgtat gtaatcggcg tcacaaaata  13320
atccccggtg actttctttt aatccaggat gaaataatat gttattataa tttttgcgat  13380
ttggtccgtt ataggaattg aagtgtgctt gcggtcgcca ccactcccat ttcataattt  13440
tacatgtatt tgaaaaataa aaatttatgg tattcaattt aaacacgtat acttgtaaag  13500
aatgatatct tgaaagaaat atagtttaaa tatttattga taaaataaca agtcaggtat  13560
tatagtccaa gcaaaaacat aaatttattg atgcaagttt aaattcagaa atatttcaat  13620
aactgattat atcagctggt acattgccgt agatgaaaga ctgagtgcga tattatggtg  13680
taatacatag cggccgggtt tctagtcacc ggttaggatc cgtttaaact cgaggctagc  13740
gcatgcacat agacacacac atcatctcat tgatgcttgg taataattgt cattagattg  13800
tttttatgca tagatgcact cgaaatcagc caattttaga caagtatcaa acggatgtga  13860
cttcagtaca ttaaaaacgt ccgcaatatg atattcatta attttatatt atctaaaaga  13920
gttaaaagag aaaaaagaaa tatgacaatt ttttctttc acatcttcta acctaaaagt  13980
atgactctat ggaggctaag tttagaaaaa gatacggatc tagggtgtgg aaacatcaat  14040
ggtcaactcc ttttatattt caatcaattg ggttttgctt tatctttaca ttttctcctt  14100
ttattttcca cgtctattca aatctacttg ttagcgggtg attactcttt tttctttat  14160 agatgccaat tatttctctc ctatgtatta aattagagta tattgtcttg aaagtgactt  14220
agtattttag tttatagtct cttaaagaac gacaccttt attcttaact ctctttatca  14280
agttttaatt taaaattatt ttaaattaag tatgcataca tatcttaata tttttcttaa  14340 ttattttaa attccctaaa tttaatgttt tcatacaatg taagagatat acatattaat  14400
tatatttaaa gataaaactt actttcctgc aataaaataa agaaaaggac agtcatacaa  14460
ttatataatt aatccagaat atttatagct tttaaacatt tattttctat caattaagta  14520
ataactttaa ataaaattaa gagtacttt ttatactcca aagaatttat ttatttcaa  14580 caaaatcgtc tgactgtttc aattgatcat tatcagccta gcataaccta aatttcattt  14640
tcaaacataa cttttggcac caaatcaccc ggcattgcaa aaaagtcttt tgcgatatga  14700
ccctccacga cgcagaacca ctgttattca ttaccatcac ttttaatcct aatttcccat  14760
acacttaccc tttccatgac atcttcaaag cctttatttt gcttttcttg tttaagctgt  14820
tttaacctaa tttcatgcat ataaacaaag agtaaagcaa aggcaaatat ttgtacgtat  14880 agttttttaga cagaaaagga aagtaaatta tagagataat gaagtttgct cttttaaatt  14940
cgtcgtgatg ttatccatca tatctaaatg cttattcctg tttttgtctt ttttctcttt  15000
taccggagtt tatttttatat aattaattaa agttagtaga tctatattct ttttcataga  15060
taatccatct tctttggagg cacatcgatc attaatcata gagttttgag aagcattatc  15120
actaaagctt caattaatta tatccaataa acggtattgg tgtatgatgt tatgatagca  15180
aatagataat ctaatctata cgagccacaa aagggcatg aactctatct cgaagaaatt  15240
ggagatgaag ggattgagat tggcaccttg tgctattatt gcccactaat catt         15294
```